(12) United States Patent
McCombie et al.

(10) Patent No.: US 11,179,105 B2
(45) Date of Patent: *Nov. 23, 2021

(54) MODULAR WRIST-WORN PROCESSOR FOR PATIENT MONITORING

(71) Applicant: SOTERA WIRELESS, INC., San Diego, CA (US)

(72) Inventors: Devin McCombie, San Diego, CA (US); Gunnar Trommer, Encinitas, CA (US); Jim Moon, San Diego, CA (US); Marshal Dhillon, San Diego, CA (US); Scott Clear, Escondido, CA (US); Julian Groeli, San Diego, CA (US)

(73) Assignee: SOTERA WIRELESS, INC., San Diego, CA (US)

( * ) Notice: Subject to any disclaimer, the term of this patent is extended or adjusted under 35 U.S.C. 154(b) by 89 days.

This patent is subject to a terminal disclaimer.

(21) Appl. No.: 16/364,147

(22) Filed: Mar. 25, 2019

(65) Prior Publication Data
US 2019/0216396 A1    Jul. 18, 2019

Related U.S. Application Data

(63) Continuation of application No. 15/263,277, filed on Sep. 12, 2016, now Pat. No. 10,238,338, which is a
(Continued)

(51) Int. Cl.
*A61B 5/00* (2006.01)
*G06F 19/00* (2018.01)
(Continued)

(52) U.S. Cl.
CPC .......... *A61B 5/6831* (2013.01); *A61B 5/0022* (2013.01); *A61B 5/0024* (2013.01);
(Continued)

(58) Field of Classification Search
CPC combination set(s) only.
See application file for complete search history.

(56) References Cited

U.S. PATENT DOCUMENTS 4,263,918 A    4/1981    Swearingen et al.
4,270,547 A    6/1981    Steffen et al.
(Continued)

FOREIGN PATENT DOCUMENTS

CN    201564472 U    9/2010
CN    201658363 U    12/2010
(Continued)

OTHER PUBLICATIONS

Extended European Search Report issued in EP 19207051 dated Mar. 16, 2020 (5 pages).
(Continued)

*Primary Examiner* — Shirley X Jian
(74) *Attorney, Agent, or Firm* — Acuity Law Group, P.C.; Michael A. Whittaker

(57) ABSTRACT

The invention provides a physiological probe that comfortably attaches to the base of the patient's thumb, thereby freeing up their fingers for conventional activities in a hospital, such as reading and eating. The probe, which comprises a separate cradle module and sensor module, secures to the thumb and measures time-dependent signals corresponding to LEDs operating near 660 and 905 nm. The cradle module, which contains elements subject to wear, is preferably provided as a disposable unit.

1 Claim, 10 Drawing Sheets

Related U.S. Application Data continuation of application No. 13/399,616, filed on Feb. 17, 2012, now Pat. No. 9,439,574.

(60) Provisional application No. 61/444,285, filed on Feb. 18, 2011.

(51) Int. Cl.

| | |
|---|---|
| *G16H 40/67* | (2018.01) |
| *G16H 50/20* | (2018.01) |
| *A61B 5/332* | (2021.01) |
| *A61B 5/024* | (2006.01) |
| *G16H 40/63* | (2018.01) |
| *A61B 5/0205* | (2006.01) |
| *A61B 5/029* | (2006.01) |
| *G06F 1/16* | (2006.01) |
| *G16H 50/30* | (2018.01) |
| *G16H 20/17* | (2018.01) |
| *A61B 5/021* | (2006.01) |
| *A61B 5/053* | (2021.01) |
| *A61B 5/08* | (2006.01) |
| *A61B 5/11* | (2006.01) |
| *A61B 5/145* | (2006.01) |

(52) U.S. Cl.
CPC ............ *A61B 5/0059* (2013.01); *A61B 5/029* (2013.01); *A61B 5/02055* (2013.01); *A61B 5/02427* (2013.01); *A61B 5/332* (2021.01); *A61B 5/6824* (2013.01); *A61B 5/6826* (2013.01); *A61B 5/742* (2013.01); *A61B 5/749* (2013.01); *A61B 5/7465* (2013.01); *G06F 1/163* (2013.01); *G06F 19/00* (2013.01); *G16H 40/63* (2018.01); *G16H 40/67* (2018.01); *G16H 50/20* (2018.01); *A61B 5/021* (2013.01); *A61B 5/02438* (2013.01); *A61B 5/053* (2013.01); *A61B 5/0816* (2013.01); *A61B 5/1116* (2013.01); *A61B 5/1118* (2013.01); *A61B 5/14542* (2013.01); *A61B 2505/03* (2013.01); *A61B 2560/045* (2013.01); *A61B 2560/0412* (2013.01); *A61B 2560/0443* (2013.01); *A61B 2562/0219* (2013.01); *A61B 2562/0238* (2013.01); *A61B 2562/222* (2013.01); *A61B 2562/227* (2013.01); *G16H 20/17* (2018.01); *G16H 50/30* (2018.01)

(56) References Cited

U.S. PATENT DOCUMENTS

| | | |
|---|---|---|
| 4,305,400 A | 12/1981 | Logan |
| 4,577,639 A | 3/1986 | Simon et al. |
| 4,582,068 A | 4/1986 | Phillipps et al. |
| 4,653,498 A | 3/1987 | New, Jr. et al. |
| 4,710,164 A | 12/1987 | Levin et al. |
| 4,722,351 A | 2/1988 | Phillipps et al. |
| 4,802,486 A | 2/1989 | Goodman et al. |
| 4,807,638 A | 2/1989 | Sramek |
| 4,905,697 A | 3/1990 | Heggs et al. |
| 5,025,791 A | 6/1991 | Niwa |
| 5,140,990 A | 8/1992 | Jones et al. |
| 5,190,038 A | 3/1993 | Polson et al. |
| 5,197,489 A | 3/1993 | Conlan |
| 5,247,931 A | 9/1993 | Norwood |
| 5,316,008 A | 5/1994 | Suga et al. |
| 5,339,818 A | 8/1994 | Baker et al. |
| 5,435,315 A | 7/1995 | McPhee et al. |
| 5,448,991 A | 9/1995 | Polson et al. |
| 5,465,082 A | 11/1995 | Chaco |
| 5,482,036 A | 1/1996 | Diab et al. |
| 5,485,838 A | 1/1996 | Ukawa et al. |
| 5,490,505 A | 2/1996 | Diab et al. |
| 5,515,858 A | 5/1996 | Myllymaki |
| 5,517,988 A | 5/1996 | Gerhard |
| 5,524,637 A | 6/1996 | Erickson |
| 5,549,650 A | 8/1996 | Bornzin et al. |
| 5,575,284 A | 11/1996 | Athan et al. |
| 5,577,508 A | 11/1996 | Medero |
| 5,588,427 A | 12/1996 | Tien |
| 5,593,431 A | 1/1997 | Sheldon |
| 5,632,272 A | 5/1997 | Diab et al. |
| 5,649,543 A | 7/1997 | Hosaka et al. |
| 5,680,870 A | 10/1997 | Hood et al. |
| 5,685,299 A | 11/1997 | Diab et al. |
| 5,709,205 A | 1/1998 | Bukta |
| 5,743,856 A | 4/1998 | Oka et al. |
| 5,766,131 A | 6/1998 | Kondo et al. |
| 5,769,785 A | 6/1998 | Diab et al. |
| 5,800,349 A | 9/1998 | Isaacson et al. |
| 5,820,550 A | 10/1998 | Polson et al. |
| 5,848,373 A | 12/1998 | Delorme et al. |
| 5,853,370 A | 12/1998 | Chance et al. |
| 5,857,975 A | 1/1999 | Golub |
| 5,865,755 A | 2/1999 | Golub |
| 5,865,756 A | 2/1999 | Peel, III |
| 5,873,834 A | 2/1999 | Yanagi et al. |
| 5,876,353 A | 3/1999 | Riff |
| 5,895,359 A | 4/1999 | Peel, III |
| 5,899,855 A | 5/1999 | Brown |
| 5,913,827 A | 6/1999 | Gorman |
| 5,919,141 A | 7/1999 | Money et al. |
| 5,941,836 A | 8/1999 | Friedman |
| 5,964,701 A | 10/1999 | Asada et al. |
| 5,964,720 A | 10/1999 | Pelz |
| 5,971,930 A | 10/1999 | Elghazzawi |
| 6,002,952 A | 12/1999 | Diab et al. |
| 6,011,985 A | 1/2000 | Athan et al. |
| 6,018,673 A | 1/2000 | Chin et al. |
| 6,036,642 A | 3/2000 | Diab et al. |
| 6,041,783 A | 3/2000 | Gruenke |
| 6,057,758 A | 5/2000 | Dempsey et al. |
| 6,067,462 A | 5/2000 | Diab et al. |
| 6,081,735 A | 6/2000 | Diab et al. |
| 6,081,742 A | 6/2000 | Amano et al. |
| 6,094,592 A | 7/2000 | Yorkey et al. |
| 6,117,077 A | 9/2000 | Del Mar et al. |
| 6,129,686 A | 10/2000 | Friedman |
| 6,157,850 A | 12/2000 | Diab et al. |
| 6,159,147 A | 12/2000 | Lichter et al. |
| 6,160,478 A | 12/2000 | Jacobsen et al. |
| 6,168,569 B1 | 1/2001 | McEwen et al. |
| 6,176,831 B1 | 1/2001 | Voss et al. |
| 6,198,394 B1 | 3/2001 | Jacobsen et al. |
| 6,198,951 B1 | 3/2001 | Kosuda et al. |
| 6,199,550 B1 | 3/2001 | Wiesmann et al. |
| 6,206,830 B1 | 3/2001 | Diab et al. |
| 6,236,872 B1 | 5/2001 | Diab et al. |
| 6,251,080 B1 | 6/2001 | Henkin et al. |
| 6,261,247 B1 | 7/2001 | Ishikawa et al. |
| 6,262,769 B1 | 7/2001 | Anderson et al. |
| 6,263,222 B1 | 7/2001 | Diab et al. |
| 6,287,262 B1 | 9/2001 | Amano et al. |
| 6,322,516 B1 | 11/2001 | Masuda et al. |
| 6,334,065 B1 | 12/2001 | Al-Ali et al. |
| 6,371,921 B1 | 4/2002 | Caro et al. |
| 6,388,240 B2 | 5/2002 | Schulz et al. |
| RE37,852 E | 9/2002 | Aso et al. |
| 6,443,890 B1 | 9/2002 | Schulze et al. |
| 6,468,222 B1 * | 10/2002 | Mault ................. A61B 5/0833 600/529 |
| 6,478,736 B1 * | 11/2002 | Mault ................. A61B 5/4866 600/300 |
| 6,480,729 B2 | 11/2002 | Schulz et al. |
| 6,491,647 B1 | 12/2002 | Bridger et al. |
| 6,503,206 B1 | 1/2003 | Li et al. |
| 6,516,218 B1 | 2/2003 | Cheng et al. |
| 6,516,289 B2 | 2/2003 | David |
| 6,526,310 B1 | 2/2003 | Carter et al. |
| 6,527,729 B1 | 3/2003 | Turcott |
| 6,541,756 B2 | 4/2003 | Schulz et al. |
| 6,544,173 B2 | 4/2003 | West et al. |

(56) References Cited

U.S. PATENT DOCUMENTS

| | | | |
|---|---|---|---|
| 6,544,174 B2 | 4/2003 | West et al. |
| 6,546,267 B1 | 4/2003 | Sugiura et al. |
| 6,551,252 B2 | 4/2003 | Sackner et al. |
| 6,584,336 B1 | 6/2003 | Ali et al. |
| 6,589,170 B1 | 7/2003 | Flach et al. |
| 6,595,929 B2 | 7/2003 | Stivoric et al. |
| 6,605,038 B1 * | 8/2003 | Teller | G16H 40/60 |
| | | | 600/300 |
| 6,606,993 B1 | 8/2003 | Wiesmann et al. |
| 6,616,606 B1 | 9/2003 | Petersen et al. |
| 6,645,154 B2 | 11/2003 | Oka |
| 6,650,917 B2 | 11/2003 | Diab et al. |
| 6,684,090 B2 | 1/2004 | Ali et al. |
| 6,694,177 B2 | 2/2004 | Eggers et al. |
| 6,699,194 B1 | 3/2004 | Diab et al. |
| 6,732,064 B1 | 5/2004 | Kadtke et al. |
| 6,745,060 B2 | 6/2004 | Diab et al. |
| 6,770,028 B1 | 8/2004 | Ali et al. |
| 6,790,178 B1 * | 9/2004 | Mault | A61B 5/1118 |
| | | | 600/300 |
| 6,811,538 B2 | 11/2004 | Westbrook et al. |
| 6,845,256 B2 | 1/2005 | Chin et al. |
| 6,850,787 B2 | 2/2005 | Weber et al. |
| 6,879,850 B2 | 4/2005 | Kimball |
| 6,893,396 B2 | 5/2005 | Schulze et al. |
| 6,912,414 B2 | 6/2005 | Tong |
| 6,934,571 B2 | 8/2005 | Wiesmann et al. |
| 6,947,781 B2 | 9/2005 | Asada et al. |
| 6,976,958 B2 | 12/2005 | Quy |
| 6,985,078 B2 | 1/2006 | Suzuki et al. |
| 6,997,882 B1 | 2/2006 | Parker et al. |
| 7,020,508 B2 * | 3/2006 | Stivoric | A61B 5/0205 |
| 7,020,578 B2 | 3/2006 | Sorensen et al. |
| 7,029,447 B2 | 4/2006 | Rantala |
| 7,041,060 B2 | 5/2006 | Flaherty et al. |
| 7,048,687 B1 | 5/2006 | Reuss et al. |
| 7,115,824 B2 | 10/2006 | Lo |
| 7,156,809 B2 | 1/2007 | Quy |
| 7,184,809 B1 | 2/2007 | Sterling et al. |
| 7,186,966 B2 | 3/2007 | Al-Ali |
| 7,194,293 B2 | 3/2007 | Baker, Jr. |
| 7,215,984 B2 | 5/2007 | Diab et al. |
| 7,215,987 B1 | 5/2007 | Sterling et al. |
| 7,225,007 B2 | 5/2007 | Al-Ali et al. |
| 7,237,446 B2 | 7/2007 | Chan et al. |
| 7,241,265 B2 | 7/2007 | Cummings et al. |
| 7,257,438 B2 | 8/2007 | Kinast |
| 7,296,312 B2 | 11/2007 | Menkedick et al. |
| 7,299,159 B2 | 11/2007 | Nanikashvili |
| 7,301,451 B2 | 11/2007 | Hastings |
| 7,314,451 B2 | 1/2008 | Halperin et al. |
| 7,351,206 B2 | 4/2008 | Suzuki et al. |
| 7,355,512 B1 | 4/2008 | Al-Ali |
| 7,373,191 B2 | 5/2008 | Delonzer et al. |
| 7,373,912 B2 | 5/2008 | Self et al. |
| 7,377,794 B2 | 5/2008 | Al-Ali et al. |
| 7,382,247 B2 | 6/2008 | Welch et al. |
| 7,383,069 B2 | 6/2008 | Ruchti et al. |
| 7,383,070 B2 | 6/2008 | Diab et al. |
| 7,384,398 B2 | 6/2008 | Gagnadre et al. |
| 7,400,919 B2 | 7/2008 | Petersen et al. |
| 7,420,472 B2 | 9/2008 | Tran |
| 7,427,926 B2 | 9/2008 | Sinclair et al. |
| 7,455,643 B1 | 11/2008 | Li et al. |
| 7,468,036 B1 | 12/2008 | Rulkov et al. |
| 7,477,143 B2 | 1/2009 | Albert |
| 7,479,890 B2 | 1/2009 | Lehrman et al. |
| 7,485,095 B2 | 2/2009 | Shusterman |
| 7,502,643 B2 | 3/2009 | Farringdon et al. |
| 7,508,307 B2 | 3/2009 | Albert |
| 7,509,131 B2 | 3/2009 | Krumm et al. |
| 7,509,154 B2 | 3/2009 | Diab et al. |
| 7,522,035 B2 | 4/2009 | Albert |
| 7,530,949 B2 | 5/2009 | Al-Ali et al. |
| 7,539,532 B2 | 5/2009 | Tran |
| 7,541,939 B2 | 6/2009 | Zadesky et al. |
| 7,542,878 B2 | 6/2009 | Nanikashvili |
| 7,586,418 B2 | 9/2009 | Cuddihy et al. |
| 7,598,878 B2 | 10/2009 | Goldreich |
| 7,602,301 B1 | 10/2009 | Stirling et al. |
| 7,616,110 B2 | 11/2009 | Crump et al. |
| 7,625,344 B2 | 12/2009 | Brady et al. |
| 7,628,071 B2 | 12/2009 | Sasaki et al. |
| 7,628,730 B1 | 12/2009 | Watterson et al. |
| 7,641,614 B2 | 1/2010 | Asada et al. |
| 7,648,463 B1 | 1/2010 | Elhag et al. |
| 7,656,287 B2 | 2/2010 | Albert et al. |
| 7,668,588 B2 | 2/2010 | Kovacs |
| 7,670,295 B2 | 3/2010 | Sackner et al. |
| 7,674,230 B2 | 3/2010 | Reisfeld |
| 7,674,231 B2 | 3/2010 | McCombie et al. |
| 7,678,061 B2 | 3/2010 | Lee et al. |
| 7,684,954 B2 | 3/2010 | Shahabdeen et al. |
| 7,689,437 B1 | 3/2010 | Teller et al. |
| 7,698,101 B2 | 4/2010 | Alten et al. |
| 7,698,830 B2 | 4/2010 | Townsend et al. |
| 7,698,941 B2 | 4/2010 | Sasaki et al. |
| 7,715,984 B2 | 5/2010 | Ramakrishnan et al. |
| 7,725,147 B2 | 5/2010 | Li et al. |
| 7,782,189 B2 | 8/2010 | Spoonhower et al. |
| 7,827,011 B2 | 11/2010 | Devaul et al. |
| 7,925,022 B2 | 4/2011 | Jung et al. |
| 7,976,480 B2 | 7/2011 | Grajales et al. |
| 7,983,933 B2 | 7/2011 | Karkanias et al. |
| 8,047,998 B2 | 11/2011 | Kolluri et al. |
| 8,082,160 B2 | 12/2011 | Collins, Jr. et al. |
| 8,137,270 B2 | 3/2012 | Keenan et al. |
| 8,167,800 B2 | 5/2012 | Ouchi et al. |
| 9,439,574 B2 * | 9/2016 | McCombie | A61B 5/0022 |
| 10,238,338 B2 * | 3/2019 | McCombie | A61B 5/6824 |
| 2001/0004234 A1 | 6/2001 | Petelenz et al. |
| 2001/0007923 A1 | 7/2001 | Yamamoto |
| 2001/0013826 A1 | 8/2001 | Ahmed et al. |
| 2002/0013517 A1 | 1/2002 | West et al. |
| 2002/0032386 A1 | 3/2002 | Sackner et al. |
| 2002/0072859 A1 | 6/2002 | Kajimoto et al. |
| 2002/0151805 A1 | 10/2002 | Sugo et al. |
| 2002/0156354 A1 | 10/2002 | Larson |
| 2002/0170193 A1 | 11/2002 | Townsend et al. |
| 2002/0183627 A1 | 12/2002 | Nishii et al. |
| 2002/0193671 A1 | 12/2002 | Ciurczak et al. |
| 2002/0193692 A1 | 12/2002 | Inukai et al. |
| 2002/0198679 A1 | 12/2002 | Victor et al. |
| 2003/0004420 A1 | 1/2003 | Narimatsu |
| 2003/0130590 A1 | 7/2003 | Bui et al. |
| 2003/0135099 A1 | 7/2003 | Al-Ali |
| 2003/0153836 A1 | 8/2003 | Gagnadre et al. |
| 2003/0158699 A1 | 8/2003 | Townsend et al. |
| 2003/0167012 A1 | 9/2003 | Friedman et al. |
| 2003/0171662 A1 | 9/2003 | O'Connor et al. |
| 2003/0181815 A1 | 9/2003 | Ebner et al. |
| 2003/0208335 A1 | 11/2003 | Unuma et al. |
| 2004/0019288 A1 | 1/2004 | Kinast |
| 2004/0030261 A1 | 2/2004 | Rantala |
| 2004/0034293 A1 | 2/2004 | Kimball |
| 2004/0034294 A1 | 2/2004 | Kimball et al. |
| 2004/0054821 A1 | 3/2004 | Warren et al. |
| 2004/0073128 A1 | 4/2004 | Hatlestad et al. |
| 2004/0077934 A1 | 4/2004 | Massad |
| 2004/0122315 A1 | 6/2004 | Krill |
| 2004/0133079 A1 | 7/2004 | Mazar et al. |
| 2004/0162466 A1 | 8/2004 | Quy |
| 2004/0162493 A1 | 8/2004 | Mills |
| 2004/0225207 A1 | 11/2004 | Bae et al. |
| 2004/0267099 A1 | 12/2004 | McMahon et al. |
| 2005/0027205 A1 | 2/2005 | Tarassenko et al. |
| 2005/0043598 A1 | 2/2005 | Goode, Jr. et al. |
| 2005/0059870 A1 | 3/2005 | Aceti |
| 2005/0070773 A1 | 3/2005 | Chin et al. |
| 2005/0113107 A1 | 5/2005 | Meunier |
| 2005/0113703 A1 | 5/2005 | Farringdon et al. |
| 2005/0119586 A1 | 6/2005 | Coyle et al. |
| 2005/0119833 A1 | 6/2005 | Nanikashvili |
| 2005/0124866 A1 | 6/2005 | Elaz et al. |

(56) References Cited

U.S. PATENT DOCUMENTS

| | | |
|---|---|---|
| 2005/0124903 A1 | 6/2005 | Roteliuk et al. |
| 2005/0149350 A1 | 7/2005 | Kerr et al. |
| 2005/0171444 A1 | 8/2005 | Ono et al. |
| 2005/0187796 A1 | 8/2005 | Rosenfeld et al. |
| 2005/0206518 A1 | 9/2005 | Welch et al. |
| 2005/0209511 A1 | 9/2005 | Heruth et al. |
| 2005/0228296 A1 | 10/2005 | Banet |
| 2005/0228298 A1 | 10/2005 | Banet et al. |
| 2005/0228301 A1 | 10/2005 | Banet et al. |
| 2005/0234317 A1 | 10/2005 | Kiani |
| 2005/0240087 A1 | 10/2005 | Keenan et al. |
| 2005/0261565 A1 | 11/2005 | Lane et al. |
| 2005/0261593 A1 | 11/2005 | Zhang et al. |
| 2005/0265267 A1 | 12/2005 | Hwang |
| 2005/0283088 A1 | 12/2005 | Bernstein |
| 2006/0036141 A1 | 2/2006 | Kamath et al. |
| 2006/0047215 A1 | 3/2006 | Newman et al. |
| 2006/0074321 A1 | 4/2006 | Kouchi et al. |
| 2006/0074322 A1 | 4/2006 | Nitzan |
| 2006/0128263 A1 | 6/2006 | Baird |
| 2006/0142648 A1 | 6/2006 | Banet et al. |
| 2006/0155589 A1 | 7/2006 | Lane et al. |
| 2006/0178591 A1 | 8/2006 | Hempfling |
| 2006/0200029 A1 | 9/2006 | Evans et al. |
| 2006/0252999 A1 | 11/2006 | Devaul et al. |
| 2006/0265246 A1 | 11/2006 | Hoag |
| 2006/0270949 A1 | 11/2006 | Mathie et al. |
| 2006/0271404 A1 | 11/2006 | Brown |
| 2006/0281979 A1 | 12/2006 | Kim et al. |
| 2007/0010719 A1 | 1/2007 | Huster et al. |
| 2007/0055163 A1 | 3/2007 | Asada et al. |
| 2007/0066910 A1 | 3/2007 | Inukai et al. |
| 2007/0071643 A1 | 3/2007 | Hall et al. |
| 2007/0094045 A1 | 4/2007 | Cobbs et al. |
| 2007/0118056 A1 | 5/2007 | Wang et al. |
| 2007/0129769 A1 | 6/2007 | Bourget et al. |
| 2007/0142715 A1 | 6/2007 | Banet et al. |
| 2007/0156456 A1 | 7/2007 | McGillin et al. |
| 2007/0161912 A1 | 7/2007 | Zhang et al. |
| 2007/0185393 A1 | 8/2007 | Zhou et al. |
| 2007/0188323 A1 | 8/2007 | Sinclair et al. |
| 2007/0193834 A1 | 8/2007 | Pai et al. |
| 2007/0208233 A1 | 9/2007 | Kovacs |
| 2007/0232867 A1 | 10/2007 | Hansmann |
| 2007/0237719 A1 | 10/2007 | Jones et al. |
| 2007/0244376 A1 | 10/2007 | Wang |
| 2007/0250261 A1 | 10/2007 | Soehren |
| 2007/0252853 A1 | 11/2007 | Park et al. |
| 2007/0255116 A1 | 11/2007 | Mehta et al. |
| 2007/0260487 A1 | 11/2007 | Bartfeld et al. |
| 2007/0265533 A1 | 11/2007 | Tran |
| 2007/0265880 A1 | 11/2007 | Bartfeld et al. |
| 2007/0270671 A1 | 11/2007 | Gal |
| 2007/0276261 A1 | 11/2007 | Banet et al. |
| 2007/0282208 A1 | 12/2007 | Jacobs et al. |
| 2007/0287386 A1 | 12/2007 | Agrawal et al. |
| 2007/0293770 A1 | 12/2007 | Bour et al. |
| 2007/0293781 A1 | 12/2007 | Sims et al. |
| 2008/0004500 A1 | 1/2008 | Cazares et al. |
| 2008/0004507 A1 | 1/2008 | Williams, Jr. et al. |
| 2008/0004904 A1 | 1/2008 | Tran |
| 2008/0027341 A1 | 1/2008 | Sackner et al. |
| 2008/0033255 A1 | 2/2008 | Essenpreis et al. |
| 2008/0039731 A1 | 2/2008 | McCombie et al. |
| 2008/0077027 A1 | 3/2008 | Allgeyer |
| 2008/0082001 A1 | 4/2008 | Hatlestad et al. |
| 2008/0101160 A1 | 5/2008 | Besson |
| 2008/0103405 A1 | 5/2008 | Banet et al. |
| 2008/0114220 A1 | 5/2008 | Banet et al. |
| 2008/0132106 A1 | 6/2008 | Burnes et al. |
| 2008/0139955 A1 | 6/2008 | Hansmann et al. |
| 2008/0146887 A1 | 6/2008 | Rao et al. |
| 2008/0146892 A1 | 6/2008 | Leboeuf et al. |
| 2008/0161707 A1 | 7/2008 | Farringdon et al. |
| 2008/0162496 A1 | 7/2008 | Postrel |
| 2008/0167535 A1 | 7/2008 | Stivoric et al. |
| 2008/0171927 A1 | 7/2008 | Yang et al. |
| 2008/0194918 A1 | 8/2008 | Kulik et al. |
| 2008/0195735 A1 | 8/2008 | Hodges et al. |
| 2008/0204254 A1 | 8/2008 | Kazuno |
| 2008/0208013 A1 | 8/2008 | Zhang et al. |
| 2008/0208273 A1 | 8/2008 | Owen et al. |
| 2008/0214963 A1 | 9/2008 | Guillemaud et al. |
| 2008/0221399 A1 | 9/2008 | Zhou et al. |
| 2008/0221404 A1 | 9/2008 | Tso |
| 2008/0262362 A1 | 10/2008 | Kolluri et al. |
| 2008/0275349 A1 | 11/2008 | Halperin et al. |
| 2008/0281168 A1 | 11/2008 | Gibson et al. |
| 2008/0281310 A1 | 11/2008 | Dunning et al. |
| 2008/0287751 A1 | 11/2008 | Stivoric et al. |
| 2008/0294019 A1 | 11/2008 | Tran |
| 2008/0319282 A1 | 12/2008 | Tran |
| 2008/0319327 A1 | 12/2008 | Banet et al. |
| 2009/0018408 A1 | 1/2009 | Ouchi et al. |
| 2009/0018409 A1 | 1/2009 | Banet et al. |
| 2009/0018453 A1 | 1/2009 | Banet et al. |
| 2009/0040041 A1 | 2/2009 | Janetis et al. |
| 2009/0054752 A1 | 2/2009 | Jonnalagadda et al. |
| 2009/0069642 A1 | 3/2009 | Gao et al. |
| 2009/0076363 A1 | 3/2009 | Bly et al. |
| 2009/0076397 A1 | 3/2009 | Libbus et al. |
| 2009/0076398 A1 | 3/2009 | Li et al. |
| 2009/0076405 A1 | 3/2009 | Amurthur et al. |
| 2009/0082681 A1 | 3/2009 | Yokoyama et al. |
| 2009/0112072 A1 | 4/2009 | Banet et al. |
| 2009/0112281 A1 | 4/2009 | Miyazawa et al. |
| 2009/0112630 A1 | 4/2009 | Collins, Jr. et al. |
| 2009/0118590 A1 | 5/2009 | Teller et al. |
| 2009/0118626 A1 | 5/2009 | Moon et al. |
| 2009/0131759 A1 | 5/2009 | Sims et al. |
| 2009/0187085 A1 | 7/2009 | Pav |
| 2009/0192366 A1 | 7/2009 | Mensinger et al. |
| 2009/0198139 A1 | 8/2009 | Lewicke et al. |
| 2009/0221937 A1 | 9/2009 | Smith et al. |
| 2009/0222119 A1 | 9/2009 | Plahey et al. |
| 2009/0227877 A1 | 9/2009 | Tran |
| 2009/0233770 A1 | 9/2009 | Vincent et al. |
| 2009/0259113 A1 | 10/2009 | Liu et al. |
| 2009/0262074 A1 | 10/2009 | Nasiri et al. |
| 2009/0264712 A1 | 10/2009 | Baldus et al. |
| 2009/0287067 A1 | 11/2009 | Dorogusker et al. |
| 2009/0295541 A1 | 12/2009 | Roof |
| 2009/0306485 A1 | 12/2009 | Bell |
| 2009/0306487 A1 | 12/2009 | Crowe et al. |
| 2009/0306524 A1 | 12/2009 | Muhlsteff et al. |
| 2009/0312973 A1 | 12/2009 | Hatlestad et al. |
| 2009/0318779 A1 | 12/2009 | Tran |
| 2009/0322513 A1 | 12/2009 | Hwang et al. |
| 2009/0326349 A1 | 12/2009 | McGonigle et al. |
| 2010/0010380 A1 | 1/2010 | Panken et al. |
| 2010/0030034 A1 | 2/2010 | Schulhauser et al. |
| 2010/0030085 A1 | 2/2010 | Rojas Ojeda et al. |
| 2010/0056881 A1 | 3/2010 | Libbus et al. |
| 2010/0056886 A1 | 3/2010 | Hurtubise et al. |
| 2010/0113948 A1 | 5/2010 | Yang et al. |
| 2010/0125188 A1 | 5/2010 | Schilling et al. |
| 2010/0130811 A1 | 5/2010 | Leuthardt et al. |
| 2010/0160793 A1 | 6/2010 | Lee et al. |
| 2010/0160794 A1 | 6/2010 | Banet et al. |
| 2010/0160795 A1 | 6/2010 | Banet et al. |
| 2010/0160796 A1 | 6/2010 | Banet et al. |
| 2010/0160797 A1 | 6/2010 | Banet et al. |
| 2010/0160798 A1 | 6/2010 | Banet et al. |
| 2010/0165589 A1 | 7/2010 | Banet et al. |
| 2010/0210930 A1 | 8/2010 | Saylor |
| 2010/0217099 A1 | 8/2010 | Leboeuf et al. |
| 2010/0222649 A1 | 9/2010 | Schoenberg |
| 2010/0234693 A1 | 9/2010 | Srinivasan et al. |
| 2010/0234786 A1 | 9/2010 | Fulkerson et al. |
| 2010/0241011 A1 | 9/2010 | McCombie et al. |
| 2010/0261988 A1* | 10/2010 | Tamir ............... A61B 5/150114 600/365 |
| 2010/0280440 A1 | 11/2010 | Skelton et al. |
| 2010/0298650 A1 | 11/2010 | Moon et al. |

(56) References Cited

U.S. PATENT DOCUMENTS

| | | |
|---|---|---|
| 2010/0298651 A1 | 11/2010 | Moon et al. |
| 2010/0298652 A1 | 11/2010 | McCombie et al. |
| 2010/0298653 A1 | 11/2010 | McCombie et al. |
| 2010/0298654 A1 | 11/2010 | McCombie et al. |
| 2010/0298655 A1 | 11/2010 | McCombie et al. |
| 2010/0298656 A1 | 11/2010 | McCombie et al. |
| 2010/0298657 A1 | 11/2010 | McCombie et al. |
| 2010/0298658 A1 | 11/2010 | McCombie et al. |
| 2010/0298659 A1 | 11/2010 | McCombie et al. |
| 2010/0298660 A1 | 11/2010 | McCombie et al. |
| 2010/0298661 A1 | 11/2010 | McCombie et al. |
| 2010/0312115 A1 | 12/2010 | Dentinger |
| 2010/0324384 A1 | 12/2010 | Moon et al. |
| 2010/0324385 A1 | 12/2010 | Moon et al. |
| 2010/0324386 A1 | 12/2010 | Moon et al. |
| 2010/0324387 A1 | 12/2010 | Moon et al. |
| 2010/0324388 A1 | 12/2010 | Moon et al. |
| 2010/0324389 A1 | 12/2010 | Moon et al. |
| 2010/0331640 A1 | 12/2010 | Medina |
| 2011/0066006 A1 | 3/2011 | Banet et al. |
| 2011/0066007 A1 | 3/2011 | Banet et al. |
| 2011/0066008 A1 | 3/2011 | Banet et al. |
| 2011/0066009 A1 | 3/2011 | Moon et al. |
| 2011/0066010 A1 | 3/2011 | Moon et al. |
| 2011/0066037 A1 | 3/2011 | Banet et al. |
| 2011/0066038 A1 | 3/2011 | Banet et al. |
| 2011/0066039 A1 | 3/2011 | Banet et al. |
| 2011/0066043 A1 | 3/2011 | Banet et al. |
| 2011/0066044 A1 | 3/2011 | Moon et al. |
| 2011/0066045 A1 | 3/2011 | Moon et al. |
| 2011/0066050 A1 | 3/2011 | Moon et al. |
| 2011/0066051 A1 | 3/2011 | Moon et al. |
| 2011/0066062 A1 | 3/2011 | Banet et al. |
| 2011/0070829 A1 | 3/2011 | Griffin et al. |
| 2011/0076942 A1 | 3/2011 | Taveau et al. |
| 2011/0093281 A1 | 4/2011 | Plummer et al. |
| 2011/0105862 A1 | 5/2011 | Gies et al. |
| 2011/0144456 A1 | 6/2011 | Muhlsteff et al. |
| 2011/0152632 A1 | 6/2011 | Le Neel et al. |
| 2011/0178375 A1 | 7/2011 | Forster |
| 2011/0224498 A1* | 9/2011 | Banet ............... A61B 5/6824 600/300 |
| 2011/0224499 A1 | 9/2011 | Banet et al. |
| 2011/0224500 A1 | 9/2011 | Banet et al. |
| 2011/0224506 A1 | 9/2011 | Moon et al. |
| 2011/0224507 A1 | 9/2011 | Banet et al. |
| 2011/0224508 A1 | 9/2011 | Moon |
| 2011/0224556 A1 | 9/2011 | Moon et al. |
| 2011/0224557 A1 | 9/2011 | Banet et al. |
| 2011/0224564 A1 | 9/2011 | Moon et al. |
| 2011/0257489 A1 | 10/2011 | Banet et al. |
| 2011/0257551 A1 | 10/2011 | Banet et al. |
| 2011/0257552 A1 | 10/2011 | Banet et al. |
| 2011/0257554 A1 | 10/2011 | Banet et al. |
| 2011/0257555 A1 | 10/2011 | Banet et al. |
| 2011/0275907 A1 | 11/2011 | Inciardi et al. |
| 2012/0065525 A1 | 3/2012 | Douniama et al. |
| 2012/0123232 A1 | 5/2012 | Najarian et al. |
| 2012/0296174 A1* | 11/2012 | McCombie ......... A61B 5/0404 600/301 |
| 2017/0224281 A1* | 8/2017 | McCombie ......... A61B 5/0022 |

FOREIGN PATENT DOCUMENTS

| | | |
|---|---|---|
| EP | 0443267 A1 | 8/1991 |
| EP | 0993803 A1 | 4/2000 |
| GB | 2329250 A | 3/1999 |
| WO | 9932030 A1 | 7/1999 |
| WO | 2006005169 A1 | 1/2006 |
| WO | 2007024777 A2 | 3/2007 |
| WO | 2007143535 A2 | 12/2007 |
| WO | 2008037820 A1 | 4/2008 |
| WO | 2008110788 A1 | 9/2008 |
| WO | 2009112981 A1 | 9/2009 |
| WO | 2010135516 A2 | 11/2010 |
| WO | 2010135518 A1 | 11/2010 |
| WO | 2010148205 A1 | 12/2010 |
| WO | 2011032132 A2 | 3/2011 |
| WO | 2011034881 A1 | 3/2011 |

OTHER PUBLICATIONS

Allen et al., Classification of a known sequence of motions and postures from accelerometry data using adapted Gaussian mixture models. Physiol. Meas. 2006;27:935-951.

Alves et al., CAN Protocol: A Laboratory Prototype for Fieldbus Applications_ XIX IMEKO World Congress Fundamental and Applied Metrology Sep. 6-11, 2009, Lisbon, Portugal. 4 pp. 454-457 ISBN 978-963-88410-0-1.

Asada et al., Active Noise Cancellation Using MEMS Accelerometers for Motion-Tolerant Wearable Bio-Sensors. Proceedings of the 26th Annual International Conference of the IEEE EMBS. San Francisco, CA, USA. Sep. 1-5, 2004:2157-2160.

Benefits of Digital Sensors. Gems Sensors. Feb. 14, 2008. Accessed online at: https://www.sensorland.com/HowPage054.html.

Bowers et al., Respiratory Rate Derived from Principal Component Analysis of Single Lead Electrocardiogram. Computers in Cardiology Conference Proceedings Sep. 2008;35:437-440.

Bussmann et al., Measuring daily behavior using ambulatory accelerometry: The Activity Monitor. Behav Res Methods Instrum Comput. Aug. 2001;33(3):349-356.

Chan et al., Noninvasive and Cuffless Measurements of Blood Pressure for Telemedicine. Proceedings of the 23rd Annual International Conference of the IEEE Engineering in Medicine and Biology Society 2001:3 pages.

Clifford et al., Measuring Tilt with Low-g Accelerometers. Freescale Semiconductor, Inc., 2005:8 pages.

Cretikos et al., The Objective Medical Emergency Team Activation Criteria: a case-control study. Resuscitation Apr. 2007;73(1):62-72.

Drinnan et al., Relation between heart rate and pulse transit time during paced respiration. Physiol. Meas. Aug. 2001;22(3): 425-432.

Espina et al., Wireless Body Sensor Network for Continuous Cuff-less Blood Pressure Monitoring. Proceedings of the 3rd IEEE-EMBS. International Summer School and Symposium on Medical Devices and Biosensors. MIT, Boston, USA, Sep. 4-6, 2006:11-15.

Fieselmann et al., Respiratory rate predicts cardiopulmonary arrest for internal medicine patients. J Gen Intern Med Jul. 1993; 8(7):354-360.

Flash et al., The Coordination of Arm Movements: An Experimentally Confirmed Mathematical Model. J Neurosci. Jul. 1985;5(7): 1688-1703.

Fung, Advisory System for Administration of Phenylephrine Following Spinal Anesthesia for Cesarean Section. Master's Thesis. University of British Columbia 2002: 119 pages.

Gallagher, Comparison of Radial and Femoral Arterial Blood Pressure in Children after Cardiopulmonary Bypass. J Clin Monit. Jul. 1985;1(3):168-171.

Goldhill et al., A physiologically-based early warning score for ward patients: the association between score and outcome. Anaesthesia Jun. 2005;60(6):547-553.

Hung et al., Estimation of Respiratory Waveform Using an Accelerometer. 5th IEEE International Symposium on Biomedical Imaging: From Nano to Macro, May 14-17, 2008:1493-1496.

Jackson, Digital Filter Design and Synthesis Using High-Level Modeling Tools. Virginia Polytechnic Institute and State University Thesis. Dec. 1999.

Jin, A Respiration Monitoring System Based on a Tri-Axial Accelerometer and an Air-Coupled Microphone. Technische Universiteit Eindhoven, University of Technology. Master's Graduation Paper, Electrical Engineering Aug. 25, 2009.

Karantonis et al., Implementation of a Real-Time Human Movement Classifier Using a Triaxial Accelerometer for Ambulatory Monitoring. IEEE Transactions on Information Technology in Biomedicine. Jan. 2006;10(1):156-167.

(56) References Cited

OTHER PUBLICATIONS

Khambete et al., Movement artefact rejection in impedance pneumography using six strategically placed electrodes. Physiol. Meas. 2000;21 :79-88.
Khan et al., Accelerometer Signal-based Human Activity Recognition Using Augmented Autoregressive Model Coefficients and Artificial w Neural Nets. 3oth Annual International Conference of the IEEE Engineering in Medicine and Biology Society. Aug. 20-24, 2008:5172-5175.
Kim et al., Two Algorithms for Detecting Respiratory Rate from ECG Signal. IFMBE Proceedings 2007;14(6) JC27:4069-4071.
Liu et al., The Changes in Pulse Transit Time at Specific Cuff Pressures during Inflation and Deflation. Proceedings of the 28th IEEE EMBS Annual International Conference New York City, USA, Aug. 30-Sep. 3, 2006:6404-6405.
Ma and Zhang, A Correlation Study on the Variabilities in Pulse Transit Time, Blood Pressure, and Heart Rate Recorded Simultaneously from Healthy Subjects. Conf Proc IEEE Eng Med Biol Soc. 2005;1 :996-999.
Mason, Signal Processing Methods for Non-Invasive Respiration Monitoring. Department of Engineering Science, University of Oxford 2002.
Mathie et al., Classification of basic daily movements using a triaxial accelerometer. Med Biol Eng Comput. Sep. 2004;42(5):679-687.
Mathie, Monitoring and Interpreting Human Movement Patterns using a Triaxial Accelerometer. Faculty of Engineenng. The University of New South Wales. PhD Dissertation. Aug. 2003: part1 pp. 1-256.
Mathie, Monitoring and Interpreting Human Movement Patterns using a Triaxial Accelerometer. Faculty of Engineenng. The University of New South Wales. PhD Dissertation. Aug. 2003: part2 pp. 256-512.
McKneely et al., Plug-and-Play and Network-Capable Medical Instrumentation and Database with a Complete Healthcare Technology Suite: MediCAN. Joint Workshop on High Confidence Medical Devices, Software, and Systems and Medical Device Plug-and-Play Interoperability. 2007:122-129.
Montgomery et al., Lifeguard—A Personal Physiological Monitor for Extreme Environments. Conf Proc IEEE Eng Med Biol Soc. 2004;3:2192-2195.
Nitzan et al., Effects of External Pressure on Arteries Distal to the Cuff During Sphygmomanometry. IEEE Transactions on Biomedical Engineering, Jun. 2005;52{6}:1120-1127.
O'Haver, Peak Finding and Measurement, Version 1.6 Oct. 26, 2006. Accessed online at: https://terpconnect.umd.edu/~toh/spectrum/PeakFindingandMeasurement.htm.
Otto et al., System Architecture of a Wireless Body Area Sensor Network for Ubiquitous Health Monitoring. Journal of Mobile Multimedia Jan. 10, 2006;1 (4):307-326.
Packet Definition. The Linux Information Project Jan. 8, 2006 http://www.linfo.org/packethtml.
Park et al., An improved algorithm for respiration signal extraction from electrocardiogram measured by conductive textile electrodes using instantaneous frequency estimation. Med Bio Eng Comput 2008;46:147-158.
Park et al., Direct Blood Pressure Measurements in Brachia! and Femoral Arteries in Children. Circulation Feb. 1970; 41 (2):231-237.
PDF-Pro for iPhone & iPod touch User Manual. ePapyrus Jul. 2009;1 :1-25 http://epapyrus.com/en/files/PDFPro%.
Poon and Zhang, Cuff-Less and Noninvasive Measurements of Arterial Blood Pressure by Pulse Transit Time. Conf Proc IEEE Eng Med Biol Soc. 2005;6:5877-5880.
Reinvuo et al., Measurement of Respiratory Rate with High-Resolution Accelerometer and EMFit Pressure Sensor. Proceedings of the 2006 IEEE Sensors Applications Symposium Feb. 7-9, 2006:192-195.
RS-232. Wikipedia Dec. 5, 2008 accessed online at: https://en.wikipedia.org/wiki/RS-232.
Scanaill et al., A Review of Approaches to Mobility Telemonitoring of the Elderly in Their Living Environment. Annals of Biomed Engineer. Apr. 2006;34(4):547-563.
Seo et al., Performance Improvement of Pulse Oximetry-Based Respiration Detection by Selective Mode Bandpass Filtering. Ergonomics and Health Aspects of Work with Computers Lecture Notes in Computer Science, 2007;4566:300-308.
Sifil et al., Evaluation of the Harmonized Alert Sensing Technology Device for Hemodynamic Monitoring in Chronic Hemodialysis Patients. ASAIO J. Nov.-Dec. 2003;49(6):667-672.
Signal Strength. Oct. 6, 2008. accessed online at: https://en.wikipedia.org/wiki/ Signal_ strength.
Soh et al., An investigation of respiration while wearing back belts. Applied Ergonomics 1997; 28(3):189-192.
Subbe et al., Effect of introducing the Modified Early Warning score on clinical outcomes, cardiopulmonary arrests and intensive care utilization in acute medical admissions. Anaesthesia Aug. 2003;58(8):797-802.
Talkowski, Quantifying Physical Activity in Community Dwelling Older Adults Using Accelerometry. University of Pittsburgh (Dissertation) 2008: 1-91.
Thongpithoonrat et al., Networking and Plug-and-Play of Bedside Medical Instruments. Conf Proc IEEE Eng Med Biol Soc. 2008;2008:1514-1517.
USB 2.0 Specification Engineering Change Notice. Oct. 20, 2000.
Vuorela et al., Two portable long-term measurement devices for ECG and bioimpedance. Second International Conference on Pervasive Computing Technologies for Healthcare. Jan. 30-Feb. 1, 2008: 169-172.
Weinhold et al., Buprenorphine alone and in combination with naloxone in non-dependent humans. Drug Alcohol Depend. Aug. 1992 ;30(3 ):263-274.
Wolf et al., Development of a Fall Detector and Classifier based on a Triaxial Accelerometer Demo Board. 2007:210-213.
Yan and Zhang, A Novel Calibration Method for Noninvasive Blood Pressure Measurement Using Pulse Transit Time. Proceedings of the 4th IEEE-EMBS International Summer School and Symposium on Medical Devices and Biosensors St Catharine's College, Cambridge, UK, Aug. 19-22, 2007.
Yang et al., Research on Multi-Parameter Physiological Monitor Based on CAN Bus. IFMBE Proceed. 2008; 19:417-419.
Zeltwanger, Controller Area Network and CANopen in Medical Equipment. Bus Briefing: Med Dev Manuf Technol. 2002:34-37.
Zislin et al., Ways of Improving the Accuracy of Arterial Pressure Oscillometry. Biomedical Engineering 2005;39(4):174-178.
Zitzmann and Schumann, Interoperable Medical Devices Due to Standardized CANopen Interfaces. Joint Workshop on High Confidence Medical Devices, Software, and Systems and Medical Device Plug-and-Play Interoperability. 2007:97-103.
Extended European Search Report and Written Opinion issued in application No. EP 10817733 dated Aug. 29, 2013.
Extended European Search Report and Written Opinion issued in application No. EP 08770884 dated Sep. 17, 2013.
International Preliminary Report on Patentability issued in PCT/US2010/039000 dated Jan. 5, 2012.
International Preliminary Report on Patentability issued in PCT/US2010/035554 dated Dec. 1, 2011.
International Search Report and Written Opinion issued in PCT/US2010/062564 dated Mar. 3, 2011.
International Search Report and Written Opinion issued in PCT/US2011/067441 dated Apr. 27, 2012.
International Search Report and Written Opinion issued in PCT/US2012/025648 dated May 29, 2012.
International Search Report and Written Opinion issued in PCT/US2012/025640 dated Jun. 29, 2012.
International Search Report and Written Opinion issued in PCT/US2011/027843 dated Jul. 22, 2011.
International Search Report and Written Opinion issued in PCT/US2011/033100 dated Jul. 20, 2011.
International Search Report and Written Opinion issued in PCT/US2010/035554 dated Sep. 23, 2010.
International Search Report and Written Opinion issued in PCT/US2010/039000 dated Sep. 7, 2010.

(56) References Cited

OTHER PUBLICATIONS

International Search Report and Written Opinion issued in PCT/US2010/035550 dated Oct. 15, 2010.
International Search Report and Written Opinion issued in PCT/US2010/048729 dated Nov. 3, 2010.
International Search Report and Written Opinion issued in PCT/US2010/048866 dated Nov. 5, 2010.
International Search Report and Written Opinion issued in PCT/US2012/064302 dated Jan. 15, 2013.
Office Action issued by SIPO in PRC Patent Application No. 2012800118426 dated Dec. 2, 2014—includes Engl lang translation.
Office Action issued by SIPO in PRC Patent Application No. 2012800118426 dated Sep. 16, 2015—includes Engl lang translation.

\* cited by examiner

Section B-B

Section C-C

MODULAR WRIST-WORN PROCESSOR FOR PATIENT MONITORING

RELATED APPLICATIONS

The present application is a continuation of U.S. patent application Ser. No. 15/263,277, filed Sep. 12, 2016, now U.S. Pat. No. 10,238,338, issued Mar. 26, 2019, which is a continuation of U.S. patent application Ser. No. 13/399,616 filed Feb. 17, 2012, now U.S. Pat. No. 9,439,574, issued Sep. 13, 2016, which claims the benefit of priority to U.S. Provisional Application No. 61/444,285, filed Feb. 18, 2011, each of which is hereby incorporated by reference, including the drawings.

BACKGROUND OF THE INVENTION

The following discussion of the background of the invention is merely provided to aid the reader in understanding the invention and is not admitted to describe or constitute prior art to the present invention.

Blood pressure is a vital sign often considered to be a good indicator of a patient's health. In critical care environments like the ICU and OR, blood pressure can be continuously monitored with an arterial catheter inserted in the patient's radial or femoral artery. Alternatively, blood pressure can be measured intermittently with a cuff using oscillometry, or manually by a medical professional using auscultation. Many patient monitors perform both the catheter and cuff-based measurements of blood pressure.

Blood pressure can also be monitored continuously with a technique called pulse transit time (PTT), defined as the transit time for a pressure pulse launched by a heartbeat in a patient's arterial system. Typical PTT measurements determine the time separating a maximum point on the QRS complex (indicating the peak of ventricular depolarization) and a foot of the PPG waveform (indicating the arriving pressure pulse). PTT depends primarily on arterial compliance, the propagation distance of the pressure pulse (which is closely approximated by the patient's arm length), and blood pressure.

PTT has been shown in a number of studies to correlate to systolic (SYS), diastolic (DIA), and mean (MAP) blood pressures. PTT can be measured with a patient monitor that includes separate modules to determine both an electrocardiogram (ECG) and SpO2. During a PTT measurement, multiple electrodes typically attach to a patient's chest to determine a time-dependent ECG component characterized by a sharp spike called the 'QRS complex'. The QRS complex indicates an initial depolarization of ventricles within the heart and, informally, marks the beginning of the heartbeat and a pressure pulse that follows. International Patent Application No. PCT/US2010/048866, which is hereby incorporated by reference in its entirety, describes a body-worn monitor that continuously measures a plurality of vital signs from a patient. The body-worn monitor features a series of sensors that attach to the patient to measure time-dependent PPG, ECG, accelerometer-based motion (ACC), oscillometric (OSC), respiratory rate (RR), and impedance pneumography (IP) waveforms. A wrist-worn microprocessor (CPU) continuously processes these waveforms to determine the patient's vital signs, degree of motion, posture and activity level. Sensors that measure these signals typically send digitized information to a wrist-worn transceiver through a serial interface, or bus, operating on a controlled area network (CAN) protocol. The CAN bus is typically used in the automotive industry, which allows different electronic systems to effectively and robustly communicate with each other with a small number of dropped packets, even in the presence of electrically noisy environments. This is particularly advantageous for ambulatory patients that may generate signals with large amounts of motion-induced noise.

It is to be understood that the invention is not limited in its application to the details of construction and to the arrangements of the components set forth in the following description or illustrated in the drawings. The invention is capable of embodiments in addition to those described and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

SUMMARY OF THE INVENTION

It is an object of the present invention to provide a body-worn data processing system for determining/monitoring physiological properties of the wearer. The system comprises a housing which contains the processor module, and a separate plastic casing which receives the housing. The processor module is sealed in a water-proof plastic fashion within the housing, which provides openings to access electrical interconnects operably connected to the processor module. During operation, the housing snaps into a separate plastic base (or "cradle"). Upon mating of the housing and the base, interface cavities, or "ports," are formed for receiving the terminal ends of data cables leading to and/or from one or more sensors which collect data related to the physiological properties of interest. The ports may also provide connection to one or more peripheral devices such as blood pressure cuffs, wireless communication hardware, etc. Insertion of a terminal end into such a port establishes electrical communication between the port's corresponding electrical interconnects and the cable, thereby permitting electrical communication between the processor module and the corresponding sensor or peripheral device. In certain embodiments, the communications between the processor, sensors, and any peripherals connected through the ports are configured as a peer-to-peer network such that each device on the network is an equally privileged, equipotent participant node which can simultaneously function as both "clients" and "servers" to the other nodes on the network.

The design described herein facilitates activities such as cleaning and disinfection of the processor module, as housing contains no openings for fluids common in the hospital, such as water and blood, to flow inside. During a cleaning process the housing may simply be detached from the cradle and then cleaned. In addition, wear components, such as the tabs described above, can be provided on the cradle such that the majority of wear components are located on an inexpensive disposable unit while the relatively more expensive electronic components provide for multiple uses. Finally, the peer-to-peer architecture permits each node to communicate with, and so synchronize as necessary, with the other nodes available on the system.

In a first aspect, the invention provides a body-worn physiological data processing system, comprising:
a housing supporting electronic circuitry, the housing providing a waterproof enclosure for the electronic circuitry, the electronic circuitry comprising:
one or more processors configured to receive data from, and export data to, one or more peripheral devices external to the housing, and to use data received from one or more peripheral devices provide signals in deriving a measurement of at least one physiological property of the wearer,
a display operably connected to the processor to display data received by the processor from one or more of the peripheral device(s), or a processed form thereof,
a power supply operably connected to the processor and display, and
one or more electrical contacts proximate to one or more openings in the housing and operably connected to the processor to provide one or more connections through which the processor receives data from, and exports data to, the one or more peripheral devices; and
(b) a base, or "cradle," configured to releasably receive the housing, wherein when the housing is inserted into the base, one or more interface cavities are formed between the base and the housing.
wherein each interface cavity is adapted to establish an operable connection between one of the peripheral device(s) and the processor through a data cable connected to the peripheral device by insertion of a connector on the data cable into the interface cavity such that electrical contacts on the connector interconnect with a corresponding electrical contact on the housing, The base and housing can be mated with a positive latch, or may be mated by a simple friction fit, or by a combination of these. In the case of a friction fit, the friction fit is preferably strong enough to prevent separation of the base and housing under the force of gravity. In certain embodiments, at least one interface cavity formed by mating of the housing and the base comprises a latch mechanism which acts to prevent separation of the base from the housing when a connector is inserted fully into the cavity. In preferred embodiments, this latch mechanism comprises at least one first recess in a wall of the interface cavity provided by the base, and at least one second recess in a wall of the interface cavity provided by the housing. The first and second recesses are configured to receive a portion of the connector when it is inserted which acts similarly to a latch bolt on a conventional lock to physically restrain separation of the base and housing until the connector is removed.

In certain embodiments, the base comprises a reclosable tape or retaining strap for reversibly fixing the data processing system to the wearer. In these embodiments, openings may be provided in the base through which such a strap can thread. Other alternatives for affixing the strap include bonding materials such as adhesives, ultrasonic welds, etc. The strap may comprise mated hook-and-loop patches or similar fastening elements such as tapes, snaps, buckles, etc., to secure the system to the wearer's body during use.

Preferably, the base is designed as a disposable component which receives an electronics housing preferably designed for multiple uses. As used herein, the term "disposable" with regard to the base refers to the characteristic that the base may be disengaged from housing in the course of normal use by the user of the system such that the electronics may be easily separated from, and need not be discarded with, the base. This can serve to place the device components of the system most susceptible to wear and cleanability issues on a disposable unit, while retaining the more expensive electronic components on an easily cleanable and reusable unit.

As noted above, the housing provides a waterproof enclosure for the electronic circuitry contained within the housing. The IP Code system defined in international standard IEC 60529 classifies the degrees of protection provided against the intrusion of solid objects (including body parts like hands and fingers), dust, accidental contact, and water in electrical enclosures. Preferably, the housing meets IEC 60529-2004 IPX7 standards, which provides that ingress of water in harmful quantity shall not be possible when the enclosure is immersed in water under up to 1 m of submersion for up to 30 minutes.

The connector may be held in the port by a friction fit, or may utilize a locking mechanism such as that of a standard RJ-45 modular connector which comprises a resilient tab which snap-fits into a recess on the housing. Removal of the connector is accomplished by simply pulling on the connector with sufficient force, or by disengaging the resilient tab from the recess prior to pulling. In preferred embodiments, a port can comprise a tab which exhibits a spring force and which flexes during insertion of a terminal end, and springs back when the terminal end is fully inserted for receiving and holding the cable in its proper orientation to establish data communication.

In certain embodiments, the processor is configured to derive a measurement of at least one physiological property of the wearer selected from the group consisting of heart rate, electrical activity of the heart, temperature, $SpO_2$, blood pressure, cardiac stroke volume, cardiac output, motion, activity, posture, pulse rate, and respiration rate. Peripheral devices such as sensors to be connected to the system are selected appropriately for the physiological properties of interest. The peripheral devices which may be pluaggbly connected to the physiological data processing system may be selected from the group consisting of a body-worn optical probe adapted to measure at least one optical signal detected after interaction with the wearer's tissue, an accelerometer, a pump module configured to inflate a blood pressure cuff, an ECG sensor, an ICG sensor, and a temperature sensor. As noted, each peripheral device is adapted to establish an operable connection with the processor through a data cable connected to the peripheral device by insertion of a connector on the data cable into the interface cavity. This data cable can carry 110 signals to and from the peripheral, and preferably also provides power to one or more peripherals from a power supply contained within the housing. By powering a peripheral from the body worn housing, the peripheral may be made lighter, less expensive, and more readily disposable. It is not necessary that each peripheral be so powered; for example a first peripheral may be controlled and powered by the physiological data processing system, while a second peripheral may be controlled by the physiological data processing system but powered by its own on-board battery.

As noted above, the communications between the processor, sensors, and any other peripherals connected through the ports are configured as a peer-to-peer network such that each device on the network is an equally privileged, equipotent participant node which can simultaneously function as both "clients" and "servers" to the other nodes on the network. In preferred embodiments, the nodes communicate through a serial interface, or bus, operating on a controlled area network (CAN) protocol. The CAN bus, which is typically used in the automotive industry, allows different electronic systems to effectively and robustly communicate with each other with a small number of dropped packets, even in the presence of electrically noisy environments. This is particularly advantageous for ambulatory patients that may generate signals with large amounts of motion-induced noise.

In certain embodiments, the physiological data processing system comprises a transceiver for wirelessly communicating with a data acquisition system external to the body-worn physiological data processing system. In these embodiments, the necessary communications hardware may be provided within the housing, or may be external, e.g., provided as a "dongle" which pluggably inserts into one of the interface cavities formed by the housing and the base, or may be provided partially within the housing and partially externally. Provision of the communications hardware as an external pluggable component can provide additional flexibility in configuration for the end user.

The system may utilize one or more electronic connectors adapted to insert into an interface cavity and which act as "keys" to unlock menus within the processing system which are not otherwise available to the user. Examples of such key connectors include "mode connectors" which enable certain special modes including, but not limited to a sleep mode (disabling the system, for example during shipping), a manufacturer mode (permitting a manufacturer to interact with the system for calibration, servicing, etc.), a demo mode (permitting the unit to display a pre-programmed demonstration), and a biomedical mode (permitting a hospital or other care site access to settings generally not available to a patient).

Advantageously, the system may also utilize one or more non-electronic "dummy" connectors adapted to insert into an interface cavity which is not in operable use. These plugs can serve to protect the structures within an interface cavity and, in the case of a system utilizing connectors to provide a latch between the base and the housing, can serve as a latch when no electrically active connector is being employed by the user.

A number of additional features may be incorporated into the electronics contained within the housing. By way of non-limiting example, the display may provide a touchscreen interface for data entry to the processor; a microphone and speaker configured for two-way voice communication may be provided; a voice over Internet protocol (VOIP) communication protocol may be provided; etc.

Mis-connection of medical devices by medical workers due to the use of common connectors across different device types is increasingly understood as both a source of patient injury and damage to equipment. Thus, in certain embodiments, the interface cavity comprises a "key" structure, and the corresponding connector is adapted to match the key structure to reduce the risk of insertion of an incompatible connector into an interface cavity. For example, the base may comprise a raised element in the wall of the interface cavity which is matched by a recess in the appropriate connector. Incompatible connectors lacking the appropriate recess and interface dimension would be physically prevented from insertion. This description is by way of example only and is non-limiting on the types of lock-and-key structures which may be used.

In related aspects, the present invention provides a base configured to releasably receive a housing supporting a processor, wherein when the housing is inserted into the base, one or more interface cavities are formed between the base and the housing, each interface cavity comprising one or more electrical contacts on the housing operably connected to the processor, and each interface cavity adapted to receive an electrical connector which makes sliding contact with the electrical contacts within the interface cavity to establish an operable connection between a peripheral device and the processor, the base comprising:

a latch mechanism at a first end of the base, the latch mechanism comprising at least one recess in a portion of the base which forms part of a first interface cavity, said first recesses configured to receive a portion of the electrical connector when inserted;

a tab on a portion of the base which forms part of the first interface cavity, the tab configured to insert into a recess on the electrical connector when inserted and thereby position the connector into a recess on a portion of the housing which forms part of the first interface cavity;

a tab at a second end of the base which is configured to insert into a corresponding opening in the housing when mated thereto;

wherein insertion of the electrical connector into the first interface cavity so that the connector is positioned into the recess on the housing prevents separation of the base from the housing until the connector is removed.

Still other embodiments are found in the following detailed description of the invention, and in the claims.

DETAILED DESCRIPTION OF THE INVENTION

Figure 1:
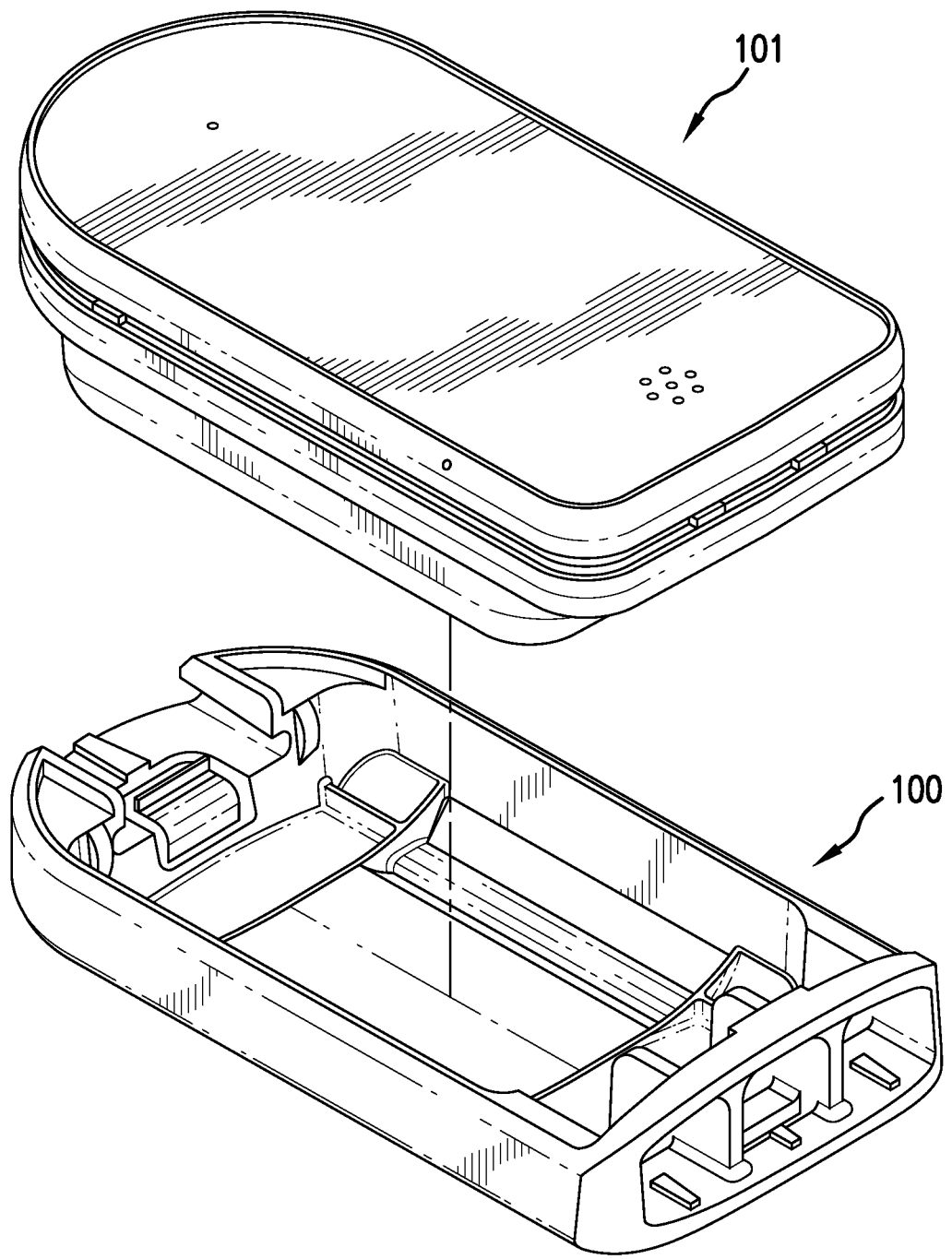
FIG. 1 shows a three-dimensional mechanical drawing of an exemplary processor module housing and base module of the present invention, depicting a mode of mating the processor module housing to the base module.
Figure 2:
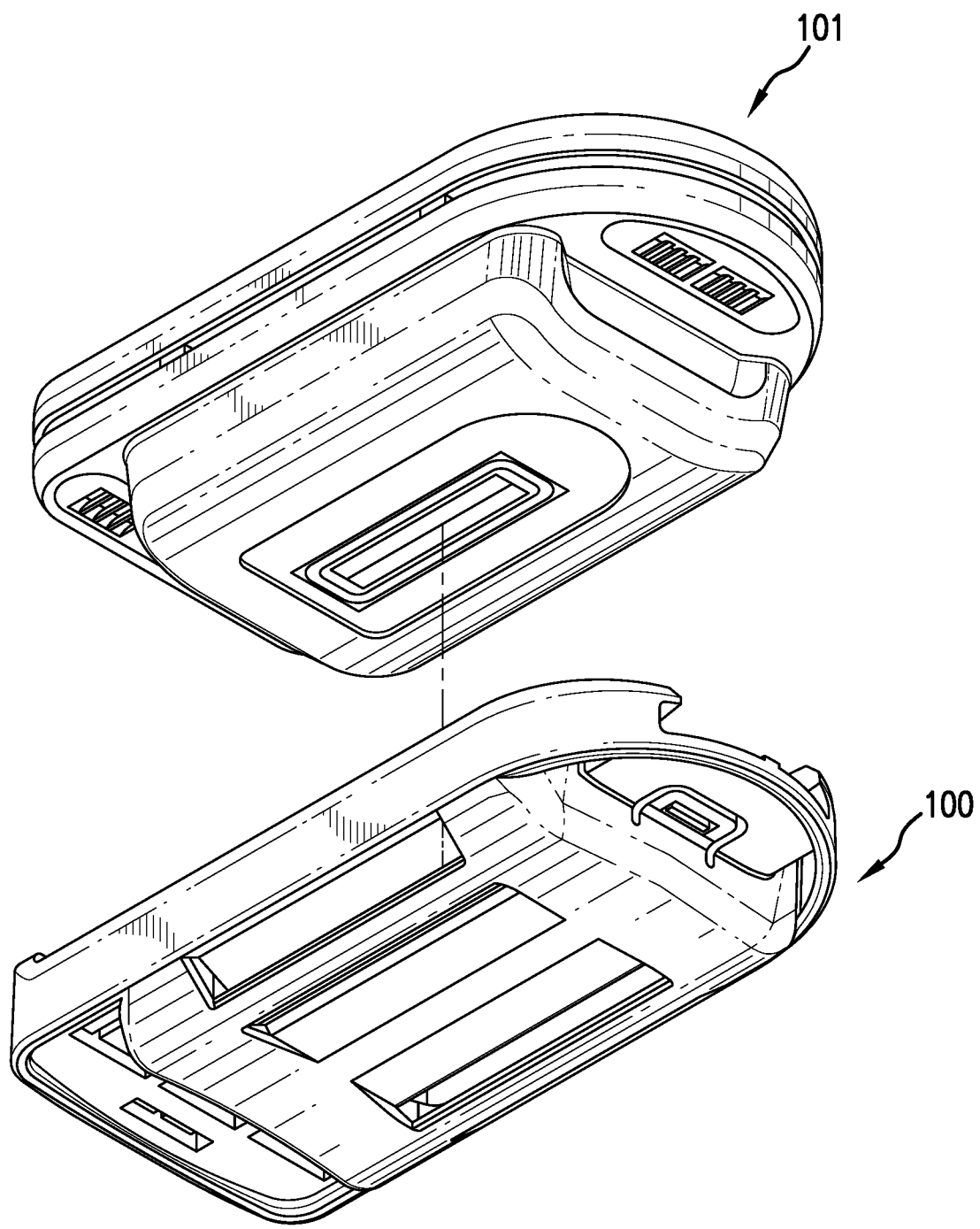
FIG. 2 shows an alternative view of a three-dimensional mechanical drawing of an exemplary processor module housing and base module of the present invention.

FIGS. 1 and 2 depict a top and bottom view of a base 100, and housing 101 which releasably attaches thereto, for use in the body-worn data processing system of the present invention. The housing provides a water-proof plastic casing housing a processor (the "system processor") and associated electronics (collectively the housing and the associated electronics being referred to herein as a "processing module"), and features openings on the underside that provide access to electrical interconnects that interface to connectors at the terminal ends of cables leading to the system's various sensors and other peripherals. In addition to being waterproof, this design facilitates activities such as cleaning and disinfection, as the housing contains no openings for fluids common in the hospital, such as water and blood, to flow inside.

The base is preferably designed as a disposable component which receives an electronics housing preferably designed for multiple uses. As used herein, the term "disposable" with regard to the base refers to the characteristic that the base may be disengaged from the housing in the course of normal use by the user of the body-worn data processing system such that the housing may be easily separated from, and need not be discarded with, the base. This can serve to place the system components most susceptible to wear and cleanability issues on a disposable unit, while retaining the more expensive electronic components in an easily cleanable and reusable unit.

During use, the housing reversibly snaps into the plastic base. Upon mating of the housing and the base, interface cavities, or "ports," are formed for receiving the terminal connectors of data cables leading to and/or from one or more peripheral devices such as sensors which collect data related to the physiological properties of interest. Insertion of a terminal connectors into such a port establishes electrical communication between the port's corresponding electrical interconnects and the cable, thereby permitting electrical communication between the system processor and the corresponding sensor or peripheral device. When mated, the housing and base are releasably attached; likewise, when a connector is inserted into a port, the connector and the port are releasably attached. As used herein, the terms "releasably attached" and "releasably receive" refers to two separate modules which may be engaged with and disengaged from one another in the course of normal use.

Figure 3:
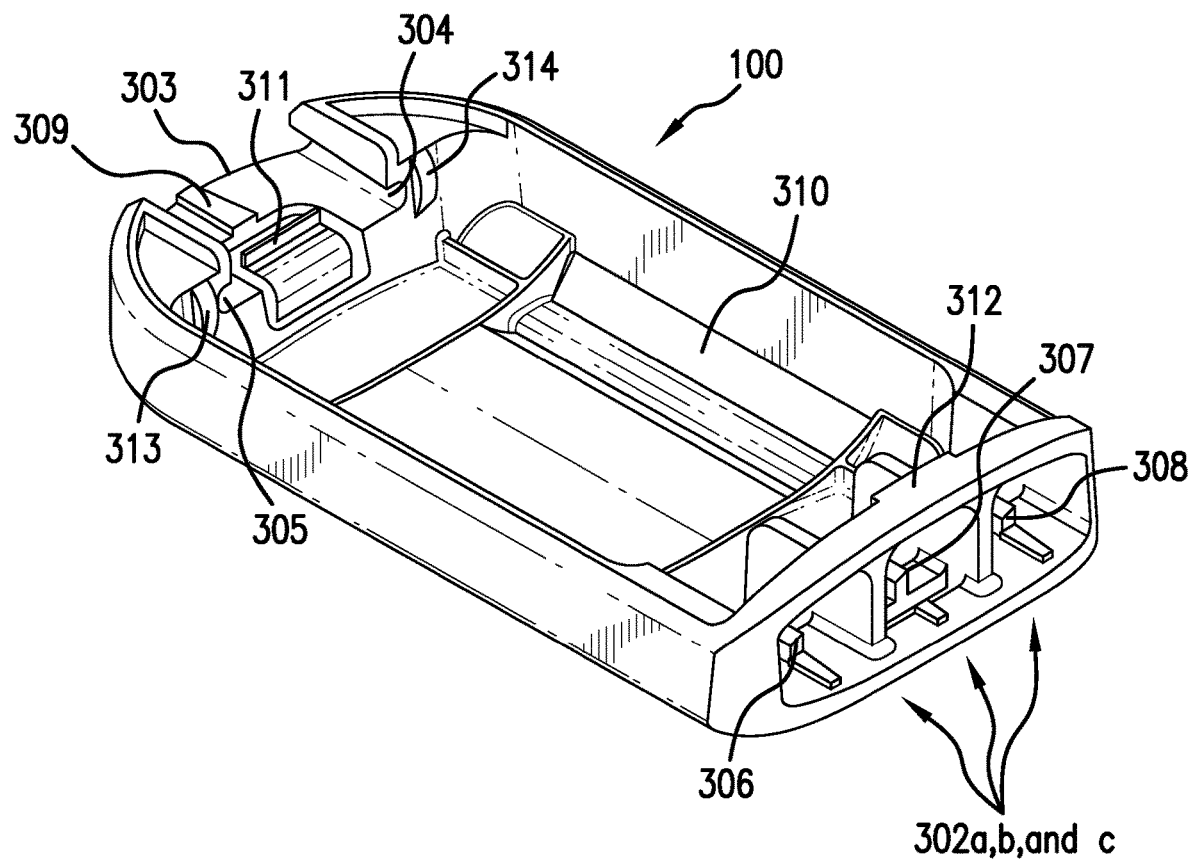
FIG. 3 shows a detailed view of a base module of the present invention.

FIGS. 3 and 4 depict base 100 in more detail. Openings 302 a, b and c positioned at a first end of the base, and a larger opening 303 positioned at a second end of the base, are configured to receive appropriately constructed terminal connectors, which are described in more detail below. The base provides a bottom wall and side walls for each interface cavity which receives a connector, while the waterproof electronics housing, when mated to the base, provides a top wall which includes electrical interconnects which are in sliding contact with the conductors of the terminal connector.

A tab 312 (also shown in cross section in FIG. 4E, 402) fits into a groove in the housing to secure the first end of the base in the housing. Raised areas 313 and 314 at the second end of the base provide a friction fit for the housing; the tightness of this friction fit may be controlled by the thickness and flexibility of these raised areas. Preferably, the friction fit is sufficiently tight that the base can be inverted with the housing in place without the housing disengaging from the base.

Opening 303 (which in this example accommodates a terminal connector having 8 electrical interconnects) is capable of receiving a larger terminal connector than are openings 302 a, b and c (which each accommodate a terminal connector having 4 electrical interconnects). Opening 303 includes in its lateral walls recesses 304 and 305 (also shown in cross section in FIGS. 4G, 404 and 405). These recesses are configured to receive extensions (FIGS. 6, 603 and 605) at the edge of the terminal connector when it is inserted into the interface cavity. A tab 311 that exhibits a spring force due to its material composition (thickness and stiffness of the material forming the tab) flexes during insertion of the terminal connector, and springs back when the terminal connector is fully inserted into the interface cavity.

Figure 8:
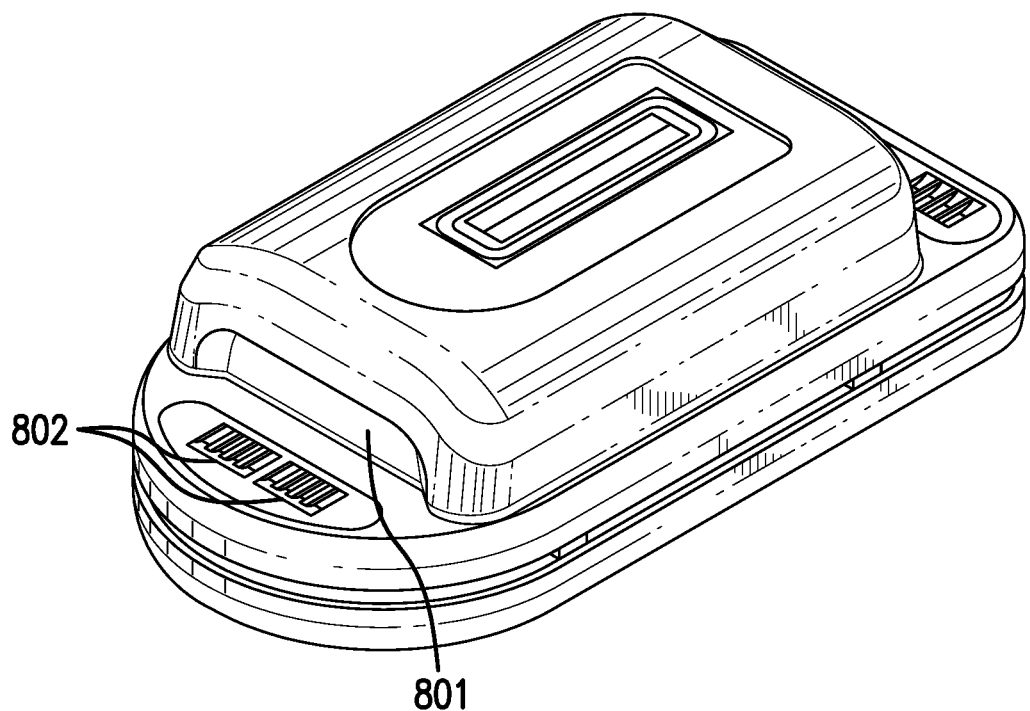
FIG. 8 shows a three-dimensional mechanical drawing depicting one view of a completed processor module housing of the present invention.

A raised portion of this tab (shown in cross-section in FIG. 4E, 401) inserts into a depression in the bottom surface of the terminal connector (FIG. 6, 602), thereby forming a detent to provide positive location of the terminal connector when in its proper position. In this position, the electrical conductors of the terminal connector are in sliding contact with the corresponding electrical interconnects on the housing, and the distal end of the terminal connector (FIG. 6, 606) is inserted into a recess in the housing (FIG. 8, 801). So inserted, the housing is secured at one end by tab 312, while at the other end the terminal connector 600 forms a "deadbolt" lock due to insertion of its distal end 606 into recess 801 and insertion of extensions 603 and 605 into lateral walls recesses 304 and 305. This "latch" prevents removal of the housing from the base until the terminal connector 600 is removed. Once the terminal connector is removed, the base and housing may be separated by simply lifting the housing from the base.

Like opening 303, each of openings 302 a, b, and c also contain a tab that flexes during insertion of the terminal connector, and springs back when the terminal connector is fully inserted into the interface cavity. A raised portion of this tab (shown in cross-section in FIG. 4E, 401) inserts into a depression in the bottom surface of the terminal connector (FIG. 5B, 504) to form a detent to provide positive location of the terminal connector when in its proper position. In this position, the electrical conductors of the terminal connector are in sliding contact with the corresponding electrical interconnects on the housing. These connectors, however, do not participate in the "latch" mechanism.

Figure 5B:
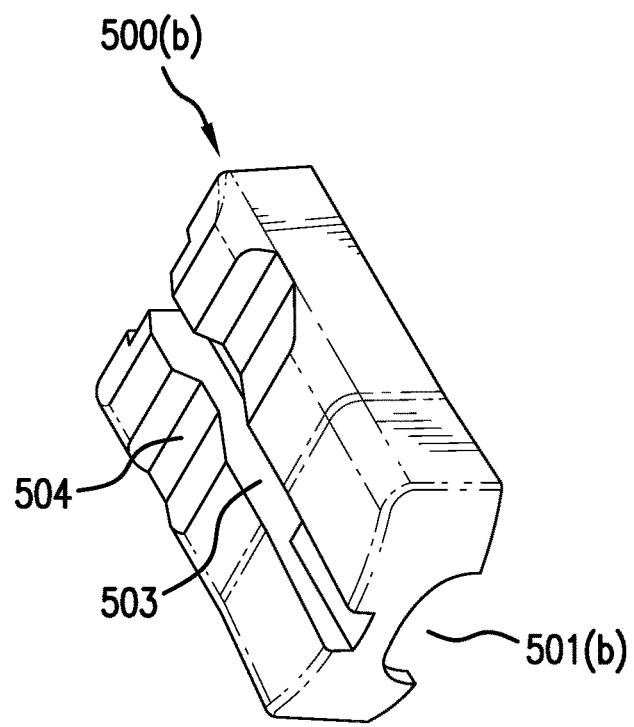
Figure 6:
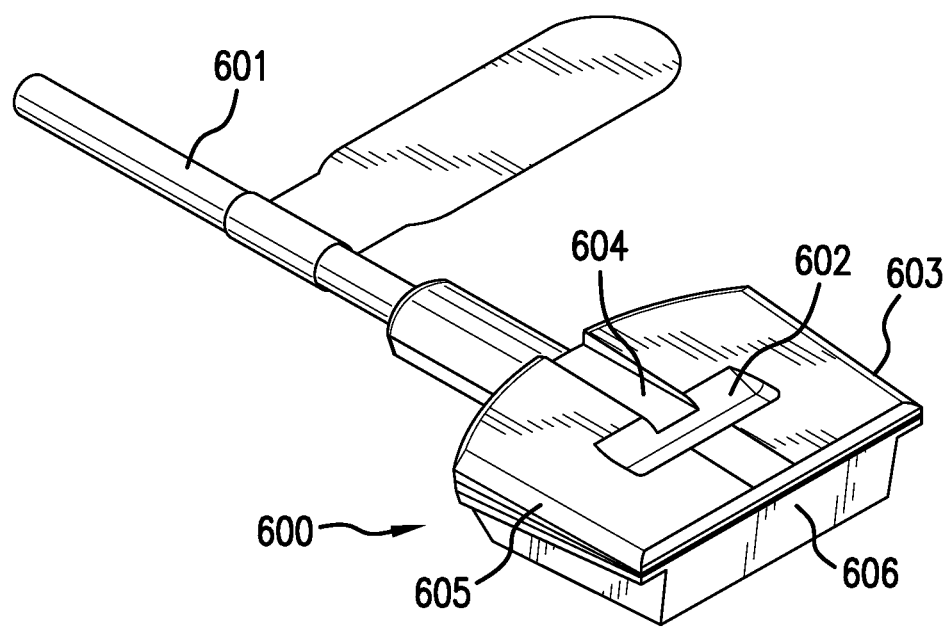
FIG. 6 shows a three-dimensional mechanical drawing of a completed connector for use in the present invention.

Raised posts 306, 307, 308, and 309 in each interface cavity provide a keying mechanism to prevent inadvertent insertion of an incompatible terminal connector. Each terminal connector has a corresponding slot (FIG. 5B, 503; FIG. 6, 604) which is adapted to receive the raised post. A similarly sized connector lacking this slot would be prevented from insertion. It is preferred that this keying mechanism be unique as compared to other electrical cable connectors used in the particular care setting to limit chances for inadvertent insertion of an incorrect cable connector.

Figure 4A:
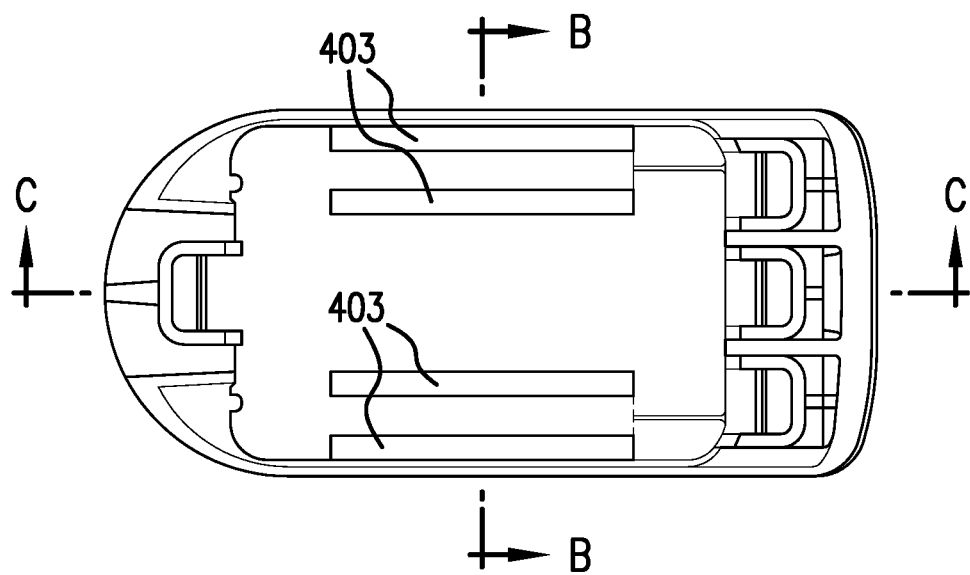
FIGS. 4A-4H show a series of sectional views of the base module shown in FIG. 3.
Figure 4B:
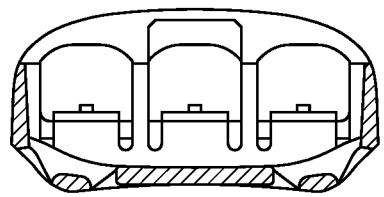
Figure 4C:
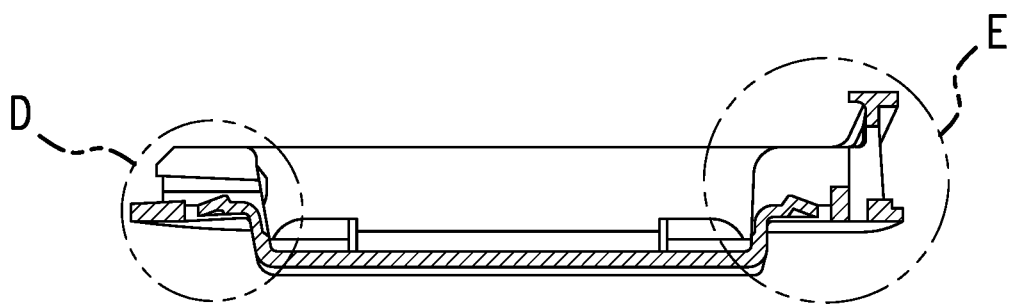
Figure 4D:
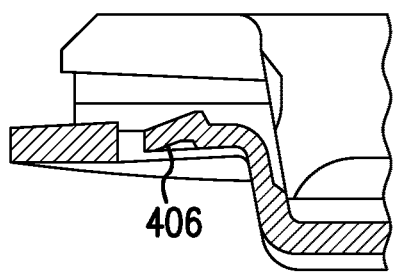
Figure 4E:
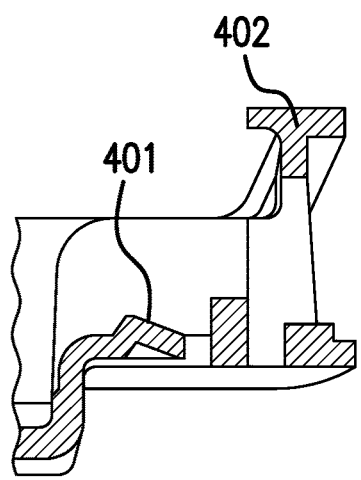
Figure 4F:
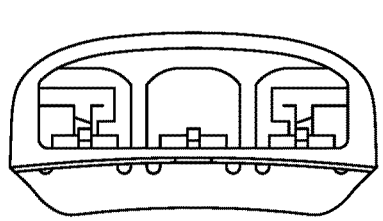
Figure 4G:
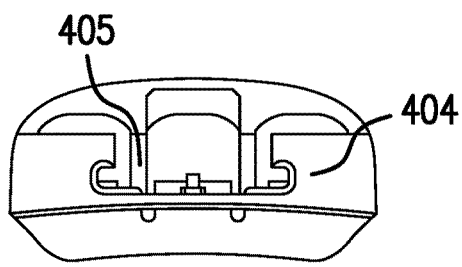
Figure 4H:
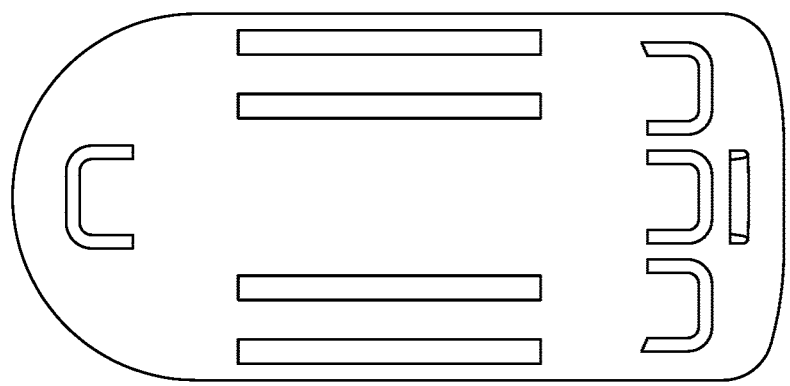

To affix the base to a wearer, slots (FIG. 3, 310; FIG. 4A, 403) are provided through which a strap may be threaded. This strap may be sized according to the body location to which the base is to be affixed. A preferred site is the wrist of the wearer.

Figure 5A:
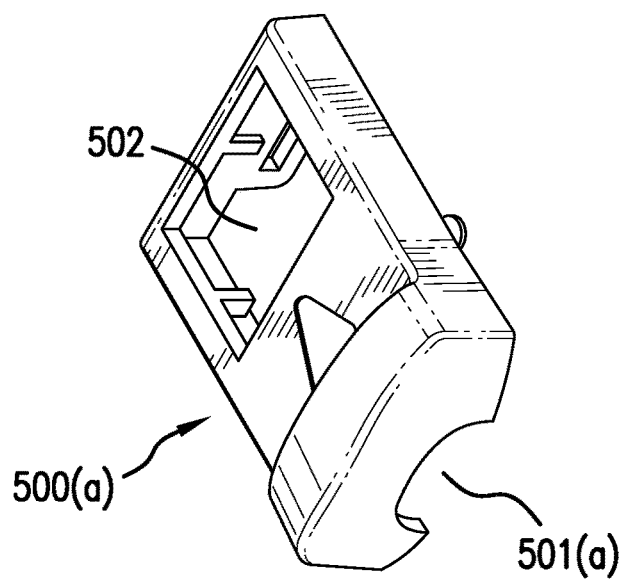
FIGS. 5A-B show a three-dimensional mechanical drawing depicting the top and bottom halves of an exemplary connector shell for use in the present invention.

FIGS. 5A and B show the top and bottom halves of a data cable connector 500 configured to insert into one of openings 302 a, b, and c without the associated cable hardware. An opening 501 allows the cable leads to pass into the connector, and spring-tension "sliding" or "wiping" electrical contacts (similar to those of a standard modular RJ-45 cable) are positioned in opening 502. The connector is conveniently made as a 2-piece component for ease of cable attachment. As noted above, slot 503 and detent recess 504 serve to position the connector in its proper orientation and in a compatible interface recess.

FIG. 6 shows the bottom surface of a completed data cable connector 600 configured to fit larger opening 303. Cable 601 extending from a peripheral (not shown) enters the connector at its proximal end, relative to distal end 606 which forms part of the latch mechanism described above. Spring-tension "sliding" or "wiping" electrical contacts are positioned on the top surface of the connector (not shown). In some cases, it may be desirable to latch the housing and base together without the use of a data cable. In this case, a "dummy" connector lacking cable 601 and the associated wiring and electrical contacts may be provided. This dummy connector will comprise slot 604, detent recess 602, distal end 606, and extensions 605 and 603 to support insertion into opening 303. As in the case of connector 600, the dummy connector will provide a latch preventing removal of the housing from the base until the dummy connector is removed.

Figure 7:
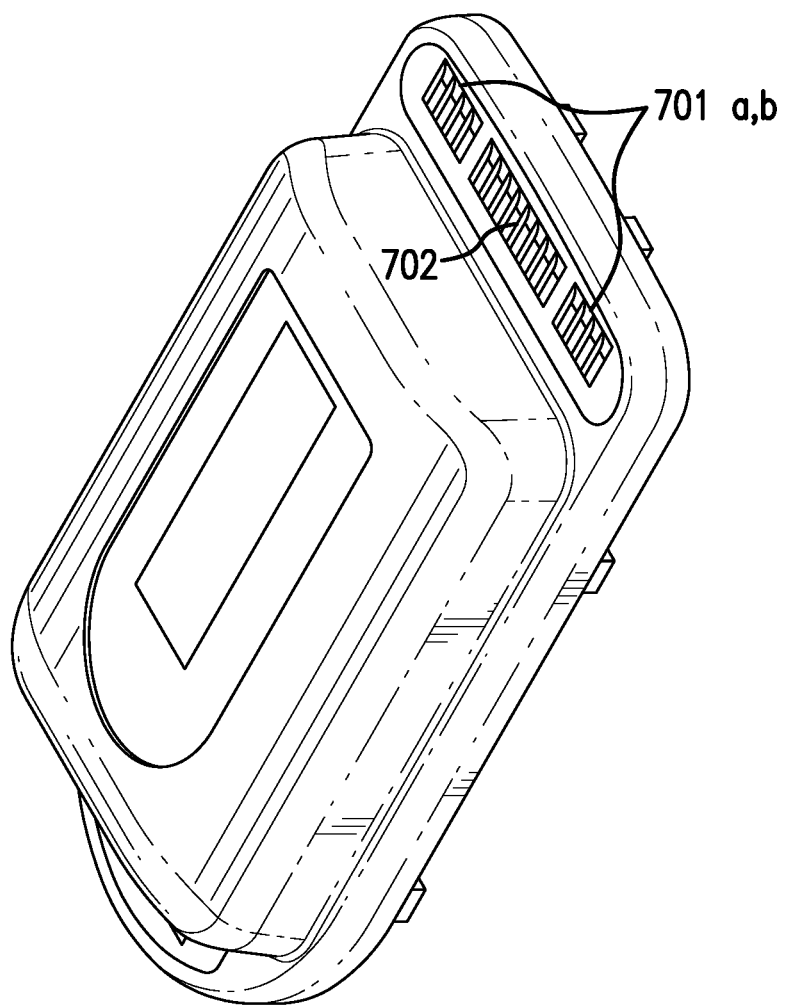
FIG. 7 shows a three-dimensional mechanical drawing depicting the bottom half of an exemplary processor module housing of the present invention.

FIGS. 7 and 8 show the underside of bottom portion of the housing. When mated to the base, contact pads 701 a and b and 702 overlay openings 302 a, b, and c in the base, thus forming the electrical interconnects that interface to the terminal connector at the end of cables. As noted above, openings 302 a, b, and c are sized to accommodate a connector having four electrical contacts, and contact pads 701 a and b contain a corresponding number of electrical interconnects. In contrast, contact pad 702 contains 8 electrical interconnects. The central four interconnects interface to the terminal end of a cable inserted into opening 302 b, and when the housing is mated to the base, the other four electrical connectors are unavailable. However, when the housing is separated from the base, these additional four contacts can provide for additional electrical access to the electronics within the housing. These additional four contacts can be used, for example, for battery charging, and a separate battery charging station which is adapted to receive the housing can be provided for this purpose.

Figure 9A:
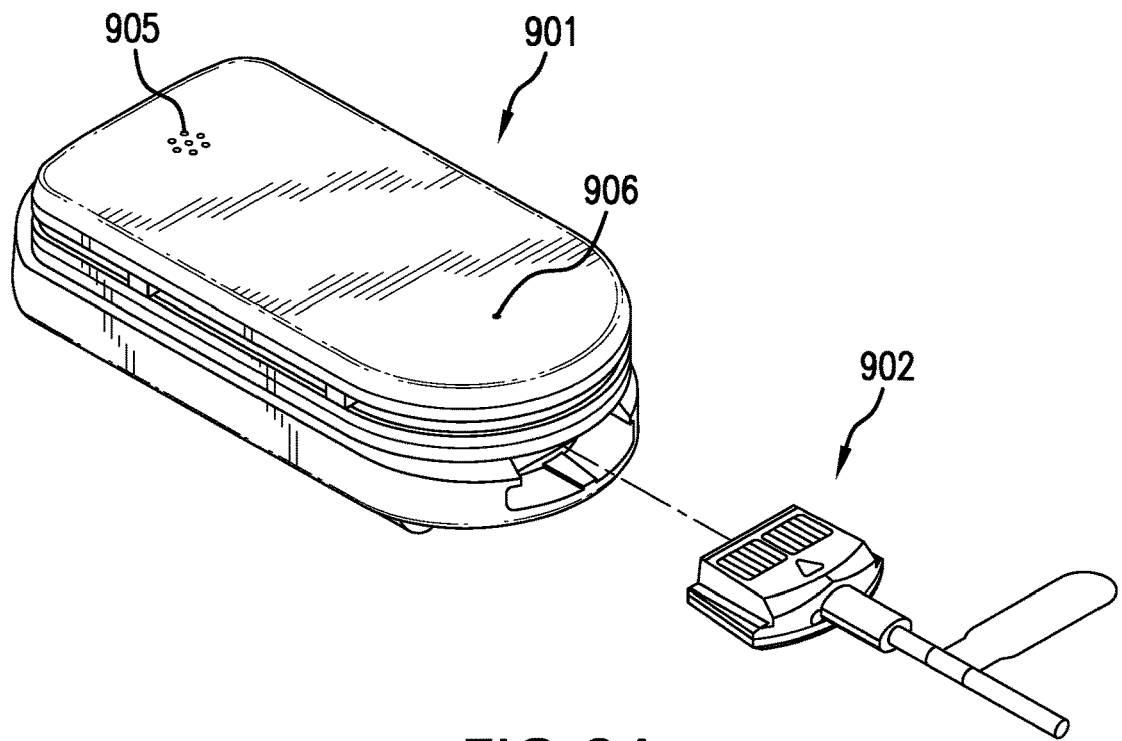
FIGS. 9A-B show a pair of three-dimensional mechanical drawings depicting the mode of insertion of a connector as shown in FIGS. 5A-B into the mated processor module housing and base module as shown in FIG. 1.
Figure 9B:
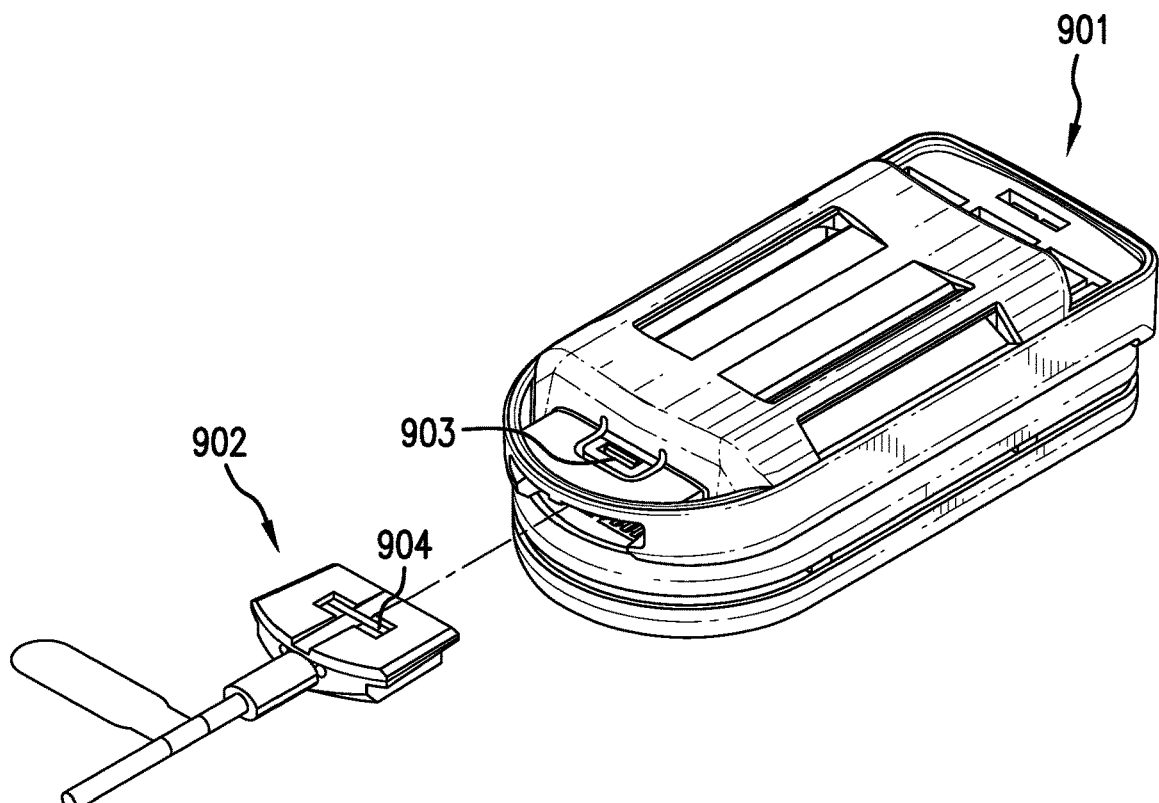

Similarly, contact pad 802 overlays opening 303 in the base, thus forming the electrical interconnects that interface to the terminal connector of the larger cable. As discussed, opening 303 is sized to accommodate a connector having eight electrical contacts, and contact pad 802 contains a corresponding number of electrical interconnects. FIG. 9A depicts the releasable insertion of connector 902 into the interface cavity formed between opening 303 and contact pad 802 when the housing is mated to the base. Connector 902 is inserted until the detent depression 904 snaps into the ridge on tab 903. At this point, the distal end of the connector is inserted into recess 801, forming the latch which retains the housing in the base until the connector is removed.

Suitable electronics to be provided within the housing is described in detail in International Patent Application No. PCT/US2010/048866, International publication WO2010/135518, U.S. publication US20090018453A1, and U.S. publication US20100168589A1, each of which is hereby incorporated by reference in its entirety. The electronics preferably support serial communication through the CAN protocol. This allows the system processor to easily interpret signals that arrive from the various sensors, and means that the interface cavities need not be associated with a specific cable; any cable can be plugged into any compatible port. Furthermore, because the CAN protocol supports peer-to-peer connection of the peripherals, these peripherals may communicate directly with one another, for example for purposes of synchronization. Digital information generated by the attached peripherals can include a header that indicates the identity or origin of the signals so that the system processor can process them accordingly.

A variety of peripheral devices may communicate with the processing module. For example, a cable may transport 110 signals to/from an ECG circuit and electrodes; accelerometers; a cuff-based system for determining blood pressure values; a glucometer; an infusion pump, a body-worn insulin pump; a ventilator; an end-tidal CO2 monitoring system; a pulse oximeter or other optical physiological probe; and a thermometer. This list is not meant to be limiting. Using one or more of these inputs, the processing system can determine one or more physiological properties associated with the wearer, such as heart rate, electrical activity of the heart, temperature, SpO2, blood pressure, cardiac stroke volume, cardiac output, medication dosage, patient weight, blood glucose levels, end tidal $CO_2$, motion, activity, posture, pulse rate, and respiration rate.

The processing module can include a speaker and/or microphone that allows a medical professional to communicate with the patient, using an appropriate protocol such as a voice over Internet protocol (VOIP). For example, the medical professional can query the patient from a central nursing station; the electronics carried within the housing may function much like a conventional cellular telephone or 'walkie talkie': the processing module can be used for voice communications with a medical professional and can additionally relay information describing the patient's vital signs and motion. The processing module can be configured via software to support speech-to-text annotations. By this is meant that speech generated externally can be converted into text for display on the processing module, and/or speech generated at the processing module can be converted into text at an external computer.

The system processor is preferably operably connected to a data input device such as a keypad or touchscreen located at the top of the housing to permit the wearer or medical personnel to interact with the system. Openings may be provided in the top of the housing for the speaker and/or microphone, as depicted in FIGS. 9A, 905 and 906; in order to maintain water resistance (e.g., at an IPX-7 standard), these openings may be sealed from underneath with a waterproof but breathable material such as a GORE-TEX® membrane (W. L. Gore & Associates, Inc.).

The electronics within the housing preferably include a battery or other power supply. Numerous battery technologies are known in the art, including common alkaline batteries, oxyride batteries, lithium batteries, etc. There are three preferred battery technologies that could be employed: Nickel Cadmium (NiCad), Nickel Metal Hydride (NiMH) and Lithium Ion (Li-ion), and most preferred are Li-ion batteries.

The battery can be provided in a "hot swap" configuration so that the electronics' data, wireless connections, etc., are preserved after the battery change. For example, prior to the hot swap a battery-powered dongle operating a firmware program may be plugged into one of the interface cavities. After being plugged in, the dongle sends a packet formatted according to the CAN protocol to the system processor indicating that its battery is about to be replaced with one having a full charge. The system processor receives the packet, and in response stores in non-volatile memory information that is normally not present when a device is initially powered on. Alternatively this information can be temporarily transferred for storage to a data buffer on an external network, or on non-volatile memory associated with the dongle. Once this is complete, the system processor can signal that the battery may be replaced. The depleted battery, located on the bottom side of the housing, can now be replaced with a charged battery. After this operation is complete the system processor can be returned to its configuration before the battery swap.

The "hot swap" configuration may not be suitable for IPX-7 standard waterproofing of the housing. Thus, in an alternative, the processor module itself may be swapped, rather than the battery within the module. In this scenario, a first processor module currently in use should transfer its store of data about the wearer to a second replacement processor module. Advantageously, a "bumping" action can be used to transfer this data. To initiate a transfer, a person accesses a special "data transfer" mode on the first and second processor modules. Then the first and second processor modules are brought into contact with one another using a sideways "bumping" action. Sensors (accelerometers) within each processor module sense the bump, and a matching algorithm pairs processor modules that detected the same bump (in terms of time and force). If and only if the bump is confirmed on the two processor modules will the data be exchanged. Following data exchange, the second processor module replaces the first processor module on the wrist-worn base of the wearer, and the first processor module is cleaned and recharged for later use. The matching algorithm may run locally on the processing modules themselves, or may run externally on a separate network. In the latter case, the processor modules would communicate the bump characteristics to the external network for processing.

Preferably, the electronics of the system support wireless transfer of data from the system to an external monitor or network. For relatively short distance RF communications, Bluetooth, Bluetooth LE, ANT+, HomeRF, IEEE 802.11x (e.g., IEEE 802.11a/b/g/n), and IEEE 802.15.4 are well known exemplary standard communications protocols that may be used. For somewhat longer range data transfers, cellular telephone protocols such as CDMA, TDMA, GSM, WAP, 3G (e.g., 3GPP, W-CDMA, TD-SCDMA, HSPA+, EVDO rev B, and CDMA2000), and 4G (e.g., LTE advanced, IEEE 802.16m) may be employed. These lists are not meant to be limiting. The electronics supporting wireless communication can be contained within the housing, or may be connected in a pluggable fashion through one of the interface cavities. Moreover, peripherals may also communicate with the system processor wirelessly rather than through a data cable connected to an interface cavity.

One skilled in the art readily appreciates that the present invention is well adapted to carry out the objects and obtain the ends and advantages mentioned, as well as those inherent therein. The examples provided herein are representative of preferred embodiments, are exemplary, and are not intended as limitations on the scope of the invention.

It will be readily apparent to a person skilled in the art that varying substitutions and modifications may be made to the invention disclosed herein without departing from the scope and spirit of the invention.

All patents and publications mentioned in the specification are indicative of the levels of those of ordinary skill in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

Other embodiments are set forth within the following claims.

What is claimed is:

1. A body-worn physiological data processing system, comprising:
    (a) a housing supporting electronic circuitry, the housing providing a waterproof enclosure for the electronic circuitry, the electronic circuitry comprising:
        a processor configured to receive data from, and export data to, one or more peripheral devices external to the housing, and to use data received from one or more peripheral devices provide signals in deriving a measurement of at least one physiological property of a wearer of the body-worn physiological data processing system,
        a display operably connected to the processor to display data received by the processor from one or more of the one or more peripheral devices, or a processed form thereof,
        a power supply operably connected to the processor and display,
        one or more electrical contacts proximate to one or more openings in the housing and operably connected to the processor to provide one or more connections through which the processor receives data from, and exports data to, the one or more peripheral devices;
    (b) a base configured to releasably receive the housing, wherein when the housing is inserted into the base, one or more interface cavities are formed between the base and the housing,
        wherein each interface cavity is adapted to releasably receive a connector on a data cable connected to at least one of the one or more peripheral devices, thereby establishing an operable connection between the one or more peripheral devices and the processor through the data cable, wherein insertion of the connector on the data cable into the interface cavity interconnects electrical contacts on the connector with corresponding electrical contacts on the housing,
        and wherein at least one interface cavity comprises a latch mechanism comprising at least one first recess in a wall thereof provided by the base, and at least one second recess in a wall thereof provided by the housing, said first and second recesses configured to receive a portion of the connector when inserted, the insertion of the connector thereby preventing separation of the base from the housing until the connector is removed;
    (c) a reclosable retaining strap for reversibly fixing the data processing system to the wearer; and
    (d) the one or more peripheral devices, wherein the one or more peripheral devices are selected from the group consisting of a body-worn optical probe adapted to measure at least one optical signal detected after interaction with the wearer's tissue, an accelerometer, a pump module configured to inflate a blood pressure cuff, an ECG sensor, an ICG sensor, and a temperature sensor.

* * * * *